US010604737B2

(12) United States Patent
Yoo

(10) Patent No.: US 10,604,737 B2
(45) Date of Patent: Mar. 31, 2020

(54) PHAGE-BASED MATRIX FOR INDUCING STEM CELL DIFFERENTIATION AND METHOD FOR PREPARING THE SAME

(71) Applicant: Pusan National University Industry-University Cooperation Foundation, Busan (KR)

(72) Inventor: So Young Yoo, Busan (KR)

(73) Assignee: Pusan National University Industry-University Cooperation Foundation, Busan (KR)

( * ) Notice: Subject to any disclaimer, the term of this patent is extended or adjusted under 35 U.S.C. 154(b) by 34 days.

(21) Appl. No.: 15/907,184

(22) Filed: Feb. 27, 2018

(65) Prior Publication Data

US 2019/0024042 A1 Jan. 24, 2019

Related U.S. Application Data

(60) Provisional application No. 62/556,040, filed on Sep. 8, 2017.

(30) Foreign Application Priority Data

Jun. 28, 2017 (KR) ........................ 10-2017-0082035

(51) Int. Cl.

| | |
|---|---|
| ***C12N 5/00*** | (2006.01) |
| ***C12N 5/078*** | (2010.01) |
| ***C07K 14/005*** | (2006.01) |
| ***C07K 9/00*** | (2006.01) |
| ***C12N 5/071*** | (2010.01) |
| ***C12N 5/074*** | (2010.01) |
| ***C12N 5/077*** | (2010.01) |
| ***C12N 7/00*** | (2006.01) |

(52) U.S. Cl.

CPC .............. *C12N 5/0068* (2013.01); *C07K 9/00* (2013.01); *C07K 14/005* (2013.01); *C12N 5/0062* (2013.01); *C12N 5/0607* (2013.01); *C12N 5/069* (2013.01); *C12N 5/0643* (2013.01); *C12N 5/0654* (2013.01); *C12N 7/00* (2013.01); *C12N 2506/03* (2013.01); *C12N 2533/40* (2013.01); *C12N 2533/50* (2013.01); *C12N 2533/90* (2013.01); *C12N 2795/00031* (2013.01); *C12N 2795/14121* (2013.01); *C12N 2795/14122* (2013.01); *C12N 2795/14131* (2013.01)

(58) Field of Classification Search

None

See application file for complete search history.

(56) References Cited

FOREIGN PATENT DOCUMENTS

KR 10-2016-0029198 * 3/2016 ............. A61K 48/00

OTHER PUBLICATIONS

Chung et al., Soft Matter, 6:4454-4459 (2010) (Year: 2010).*
Engler et al., Cell, 126:677-689 (2006) (Year: 2006).*
Lv et al., Stem Cell Res. Ther., 6:103 (2015) (Year: 2015).*
Shin et al., Biomater Res., 18(14) (2014) (Year: 2014).*
Wang et al., Biomater., 31:8608-8616 (2010) (Year: 2010).*
Yoo, Engineered Phage Based Matrix Stiffness Modulating Osteogenic Differentiation, Session No. S36-05, 2016 TERMIS AP, Taipei, Taiwan, Sep. 3-6, 2016, 2 pages.
Smith et al., Libraries of Peptides and Proteins Displayed on Filamentous Phage, Methods Enzymol. 1993;217:228-57.
Ackermann, Frequency of morphological phage descriptions in the year 2000. Brief review., Arch Virol. 2001;146(5):843-57.
Lee et al., Engineered Phage Matrix Stiffness-Modulating Osteogenic Differentiation, ACS Appl Mater Interfaces. Feb. 7, 2018;10(5):4349-4358.
Yoo et al., Facile growth factor immobilization platform based on engineered phage matrices, Soft Matter, 2011, 7(5): 1660-1666.
Yoo et al., Engineered phage nanofibers induce angiogenesis, Nanoscale. Nov. 9, 2017;9(43):17109-17117.
Merzlyak et al., Genetically engineered nanofiber-like viruses for tissue regenerating materials, Nano Lett. Feb. 2009;9(2):846-52.
Yoo et al., Synthetic Phage for Tissue Regeneration, Mediators of Inflammation, .vol. 2014 (2014), Article ID 192790.

* cited by examiner

*Primary Examiner* — Thomas J. Visone

(74) *Attorney, Agent, or Firm* — Tulip Mahaseth; Bret E. Field; Bozicevic, Field & Francis LLP

(57) ABSTRACT

The present disclosure relates to a phage-based matrix for inducing stem cell differentiation and a method for preparing the same. More specifically, the present disclosure relates to a composition for inducing differentiation of stem cells, which includes a phage-based matrix in which a gradient of stiffness is controlled by crosslinking a recombinant phage with a polymer, and a method for preparing a phage-based matrix for stem cell differentiation. According to the present invention, the method of the present disclosure provides a physical and mechanical niche environment created by the formation of a nanofibrous structure of the phage whose stiffness is controlled, thereby promoting the differentiation of stem cells into target cells. Therefore, it can be applied to a tissue matrix platform as a variety of conventional tissue engineering materials.

5 Claims, 20 Drawing Sheets

Specification includes a Sequence Listing.

[FIG. 1A]
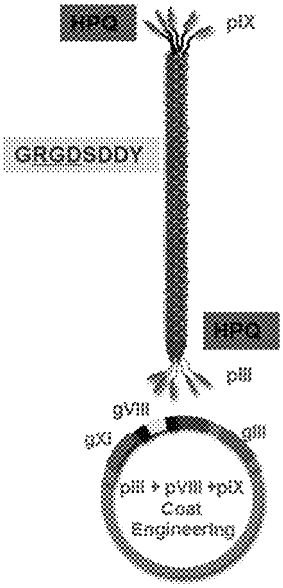

[FIG. 1B]
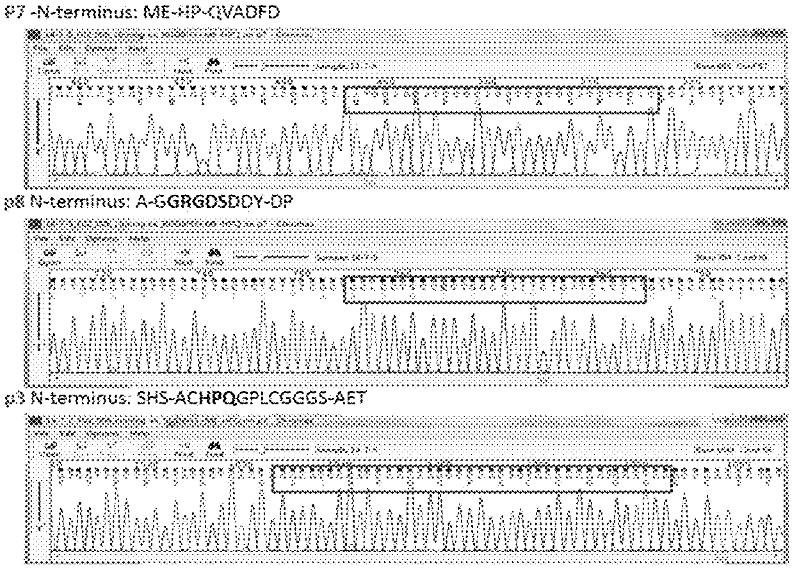

[FIG. 1C]
P9 -C-terminus: METS-HPQ-S
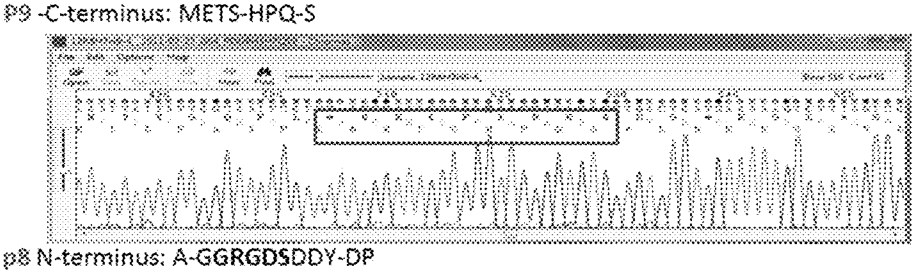
p8 N-terminus: A-GGRGDSDDY-DP
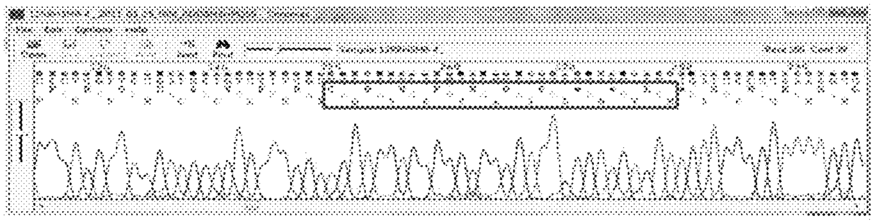
p3 N-terminus: SHS-ACHPQGPLCGGGS-AET
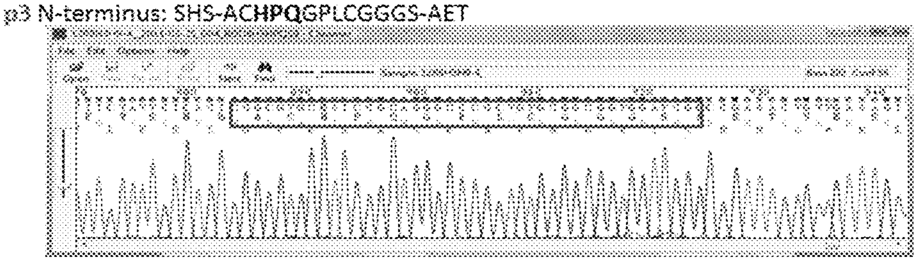

[FIG. 2]
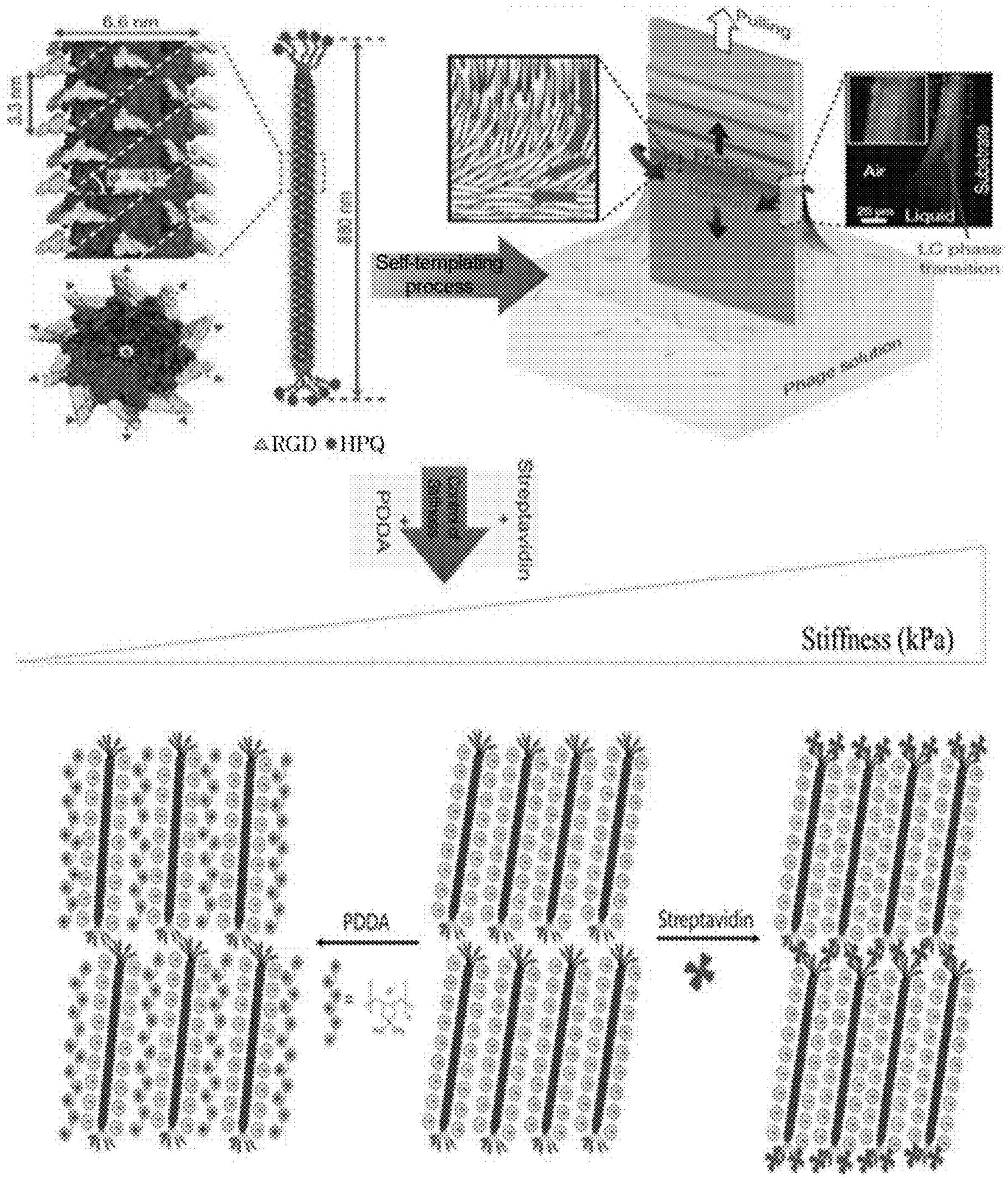

[FIG. 3]
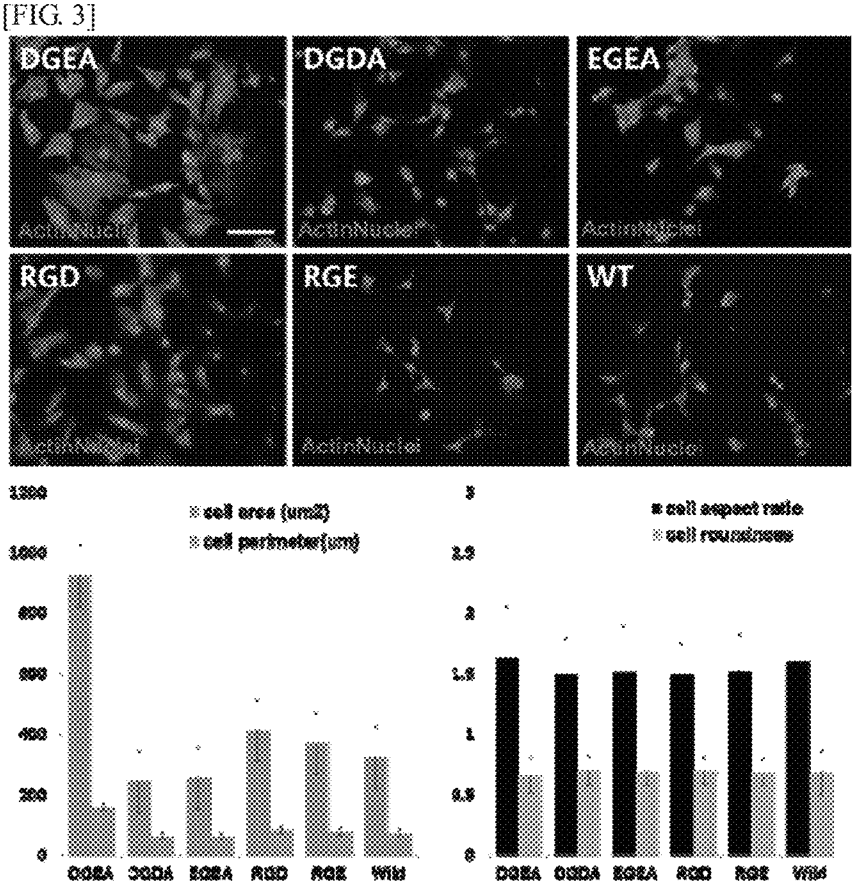

[FIG. 4]
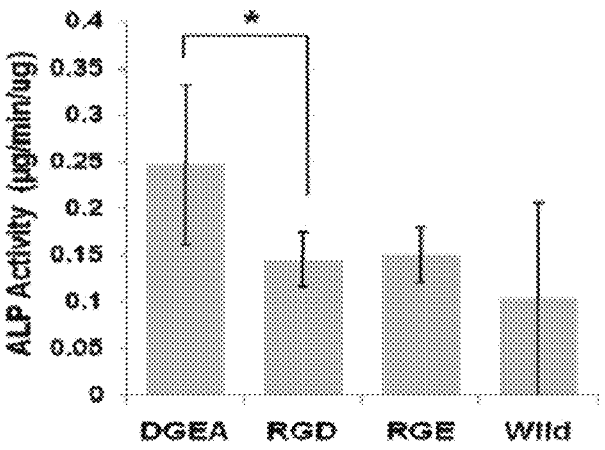

[FIG. 5]
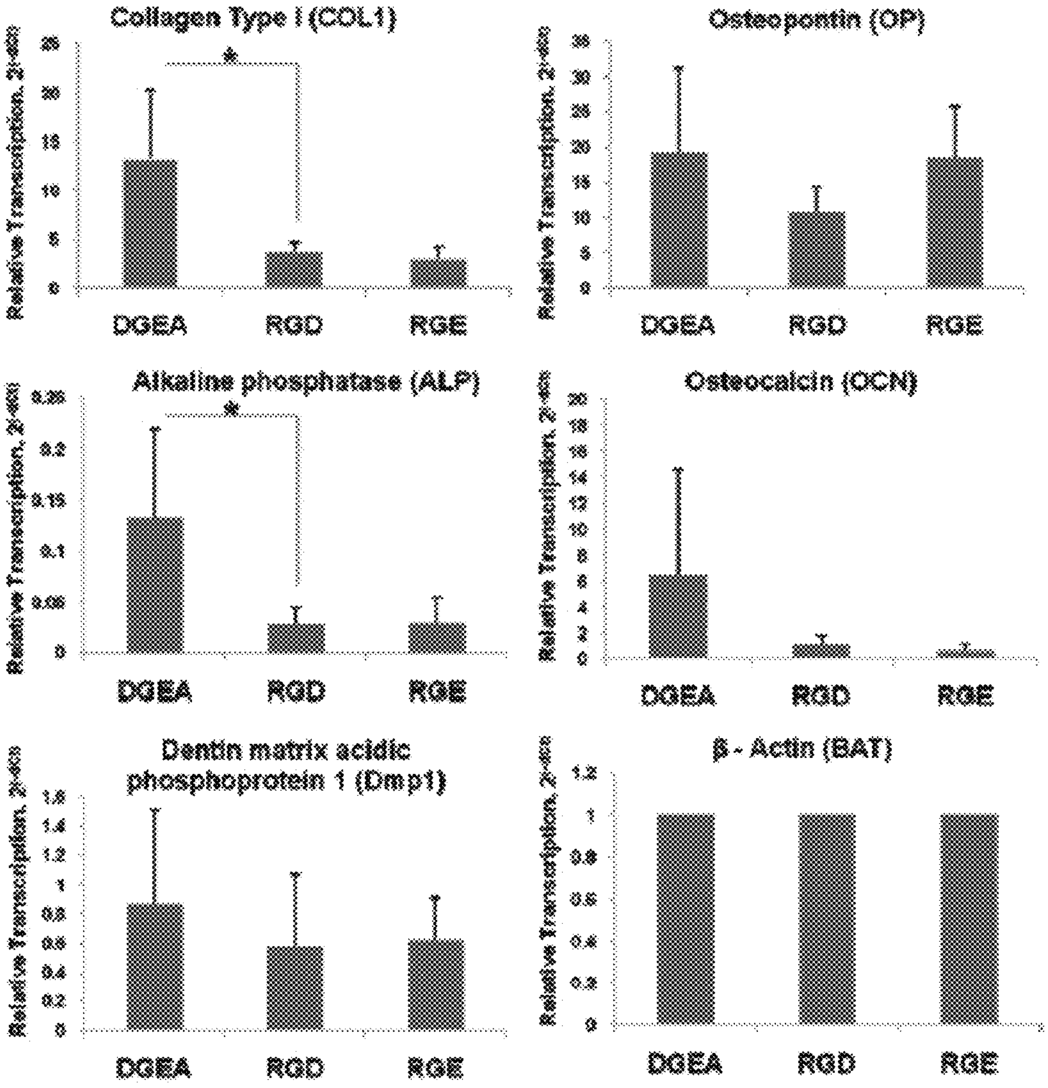

[FIG. 6]
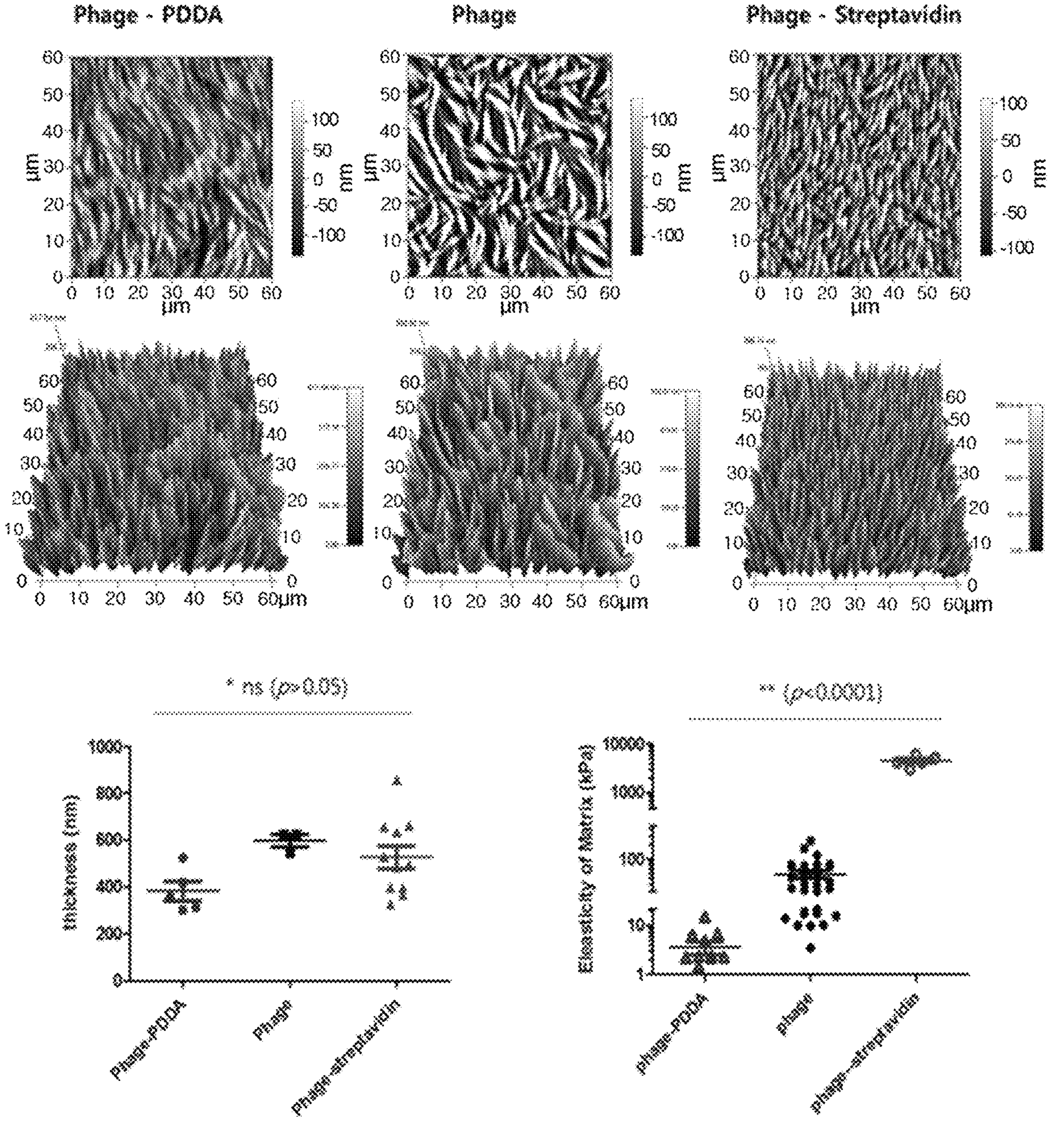

[FIG. 7A]
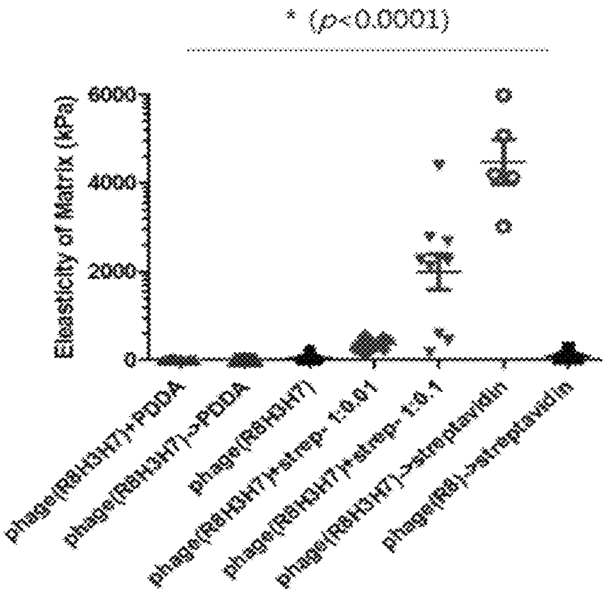

[FIG. 7B]
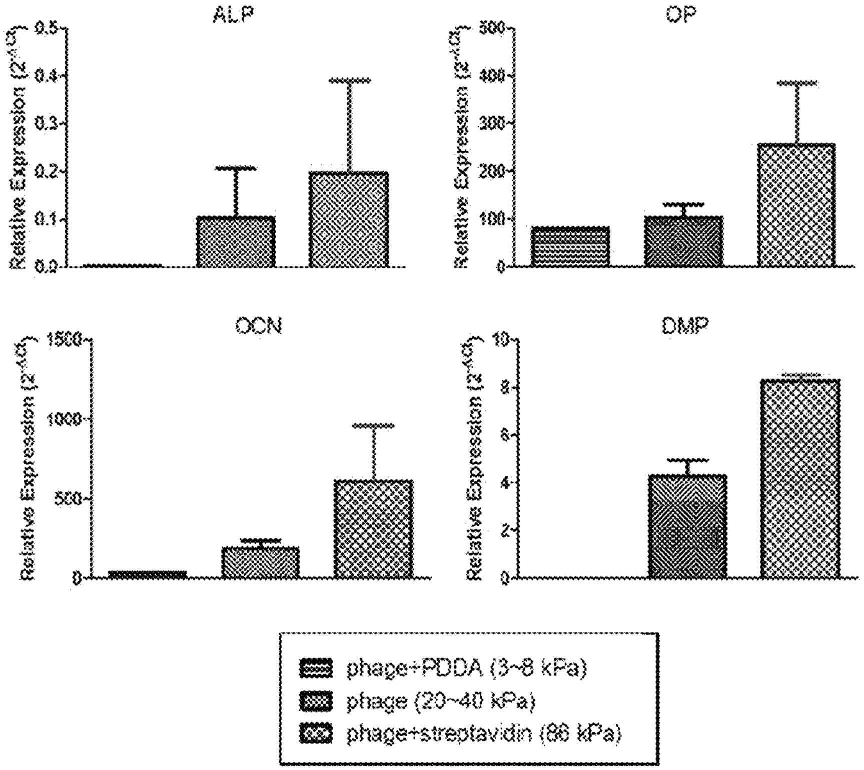

[FIG. 8]
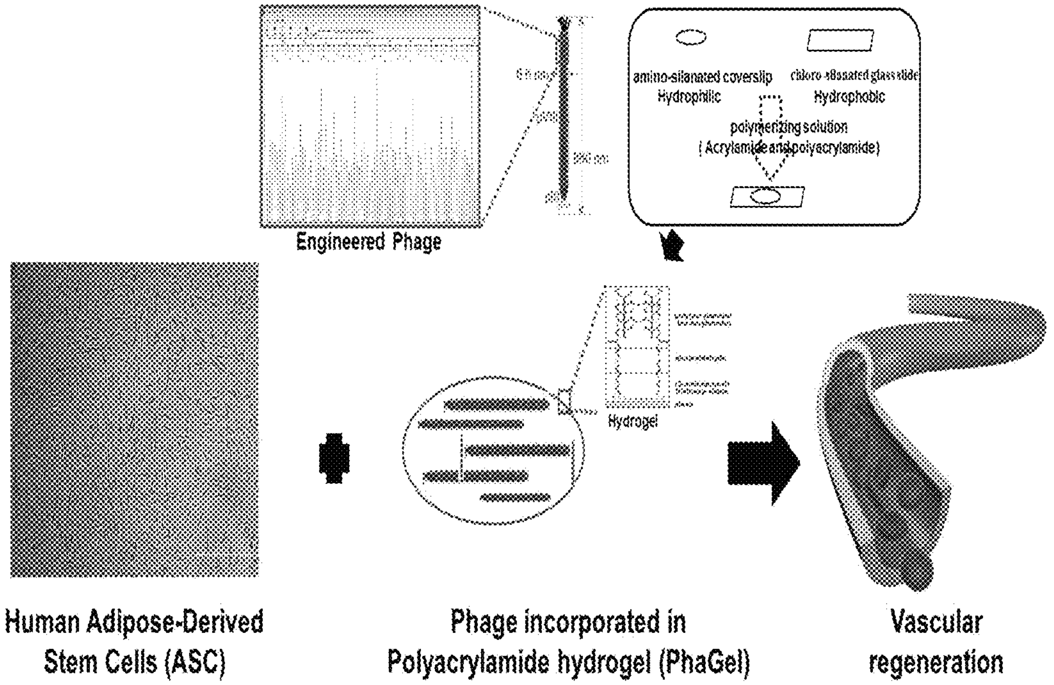

[FIG. 9]
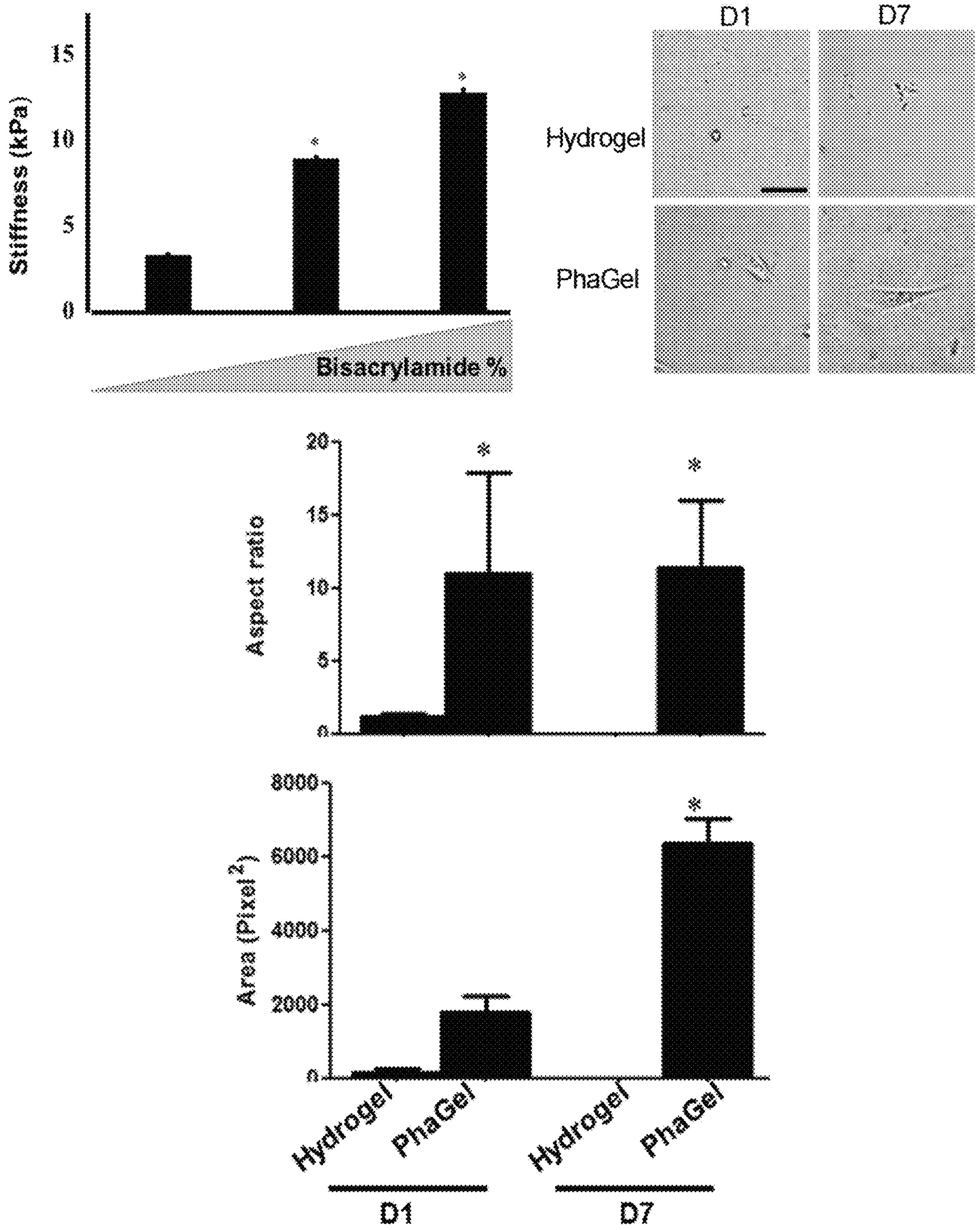

[FIG. 10]
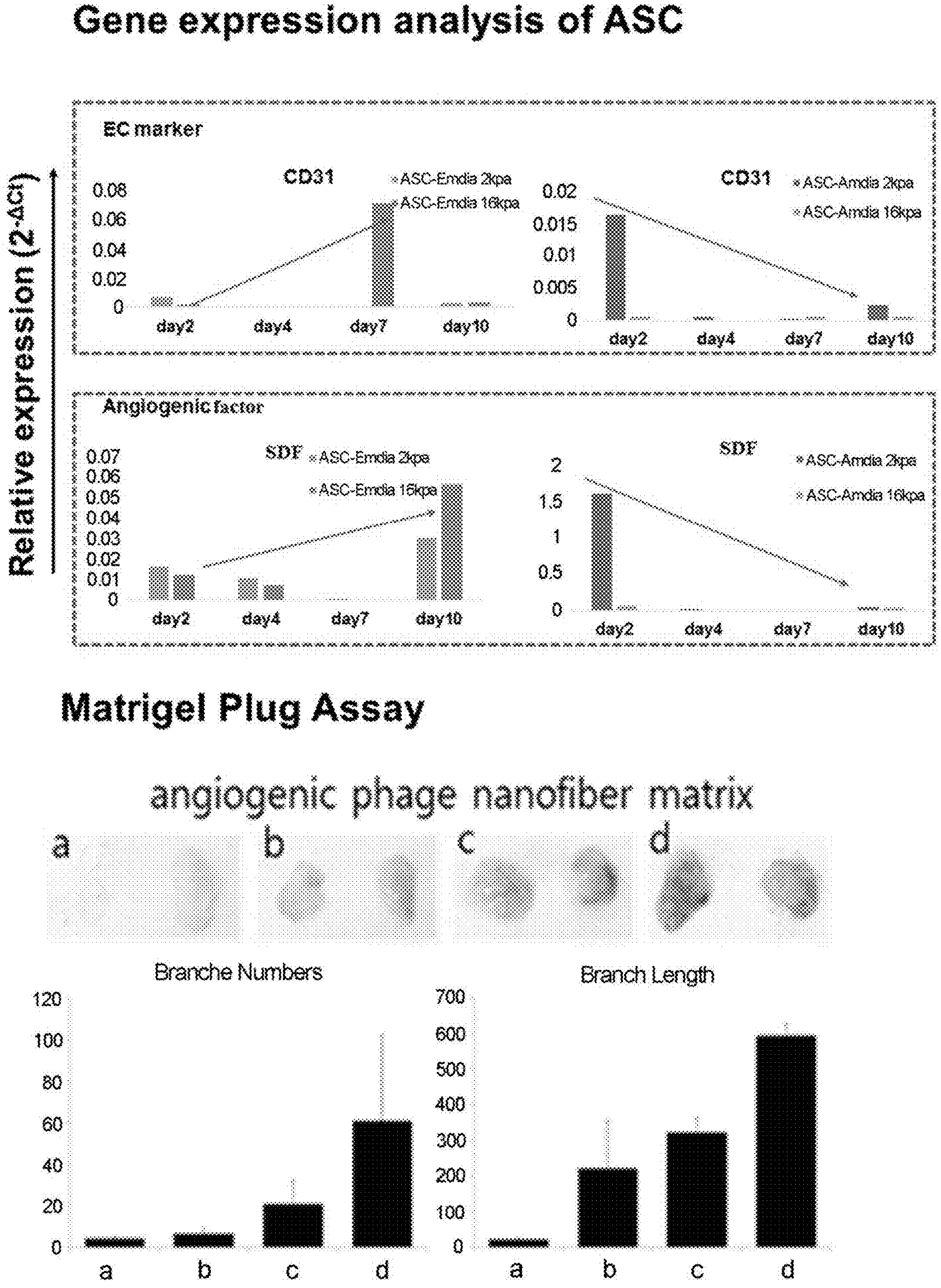

[FIG. 11A]
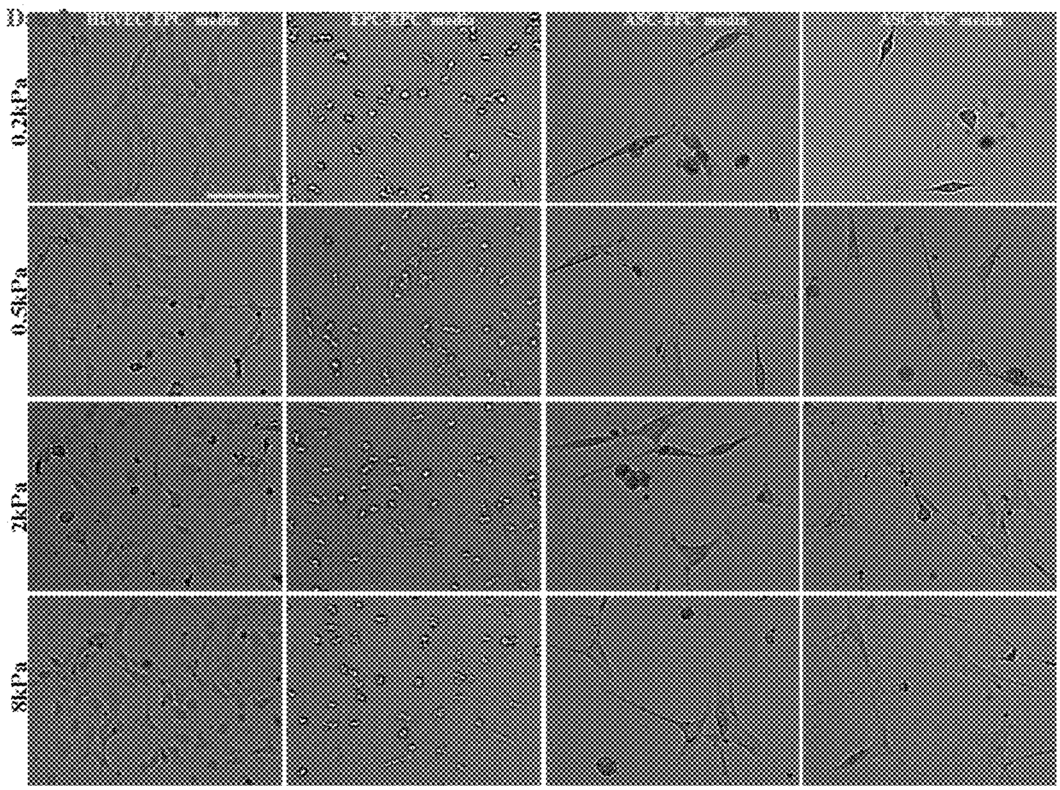

[FIG. 11B]
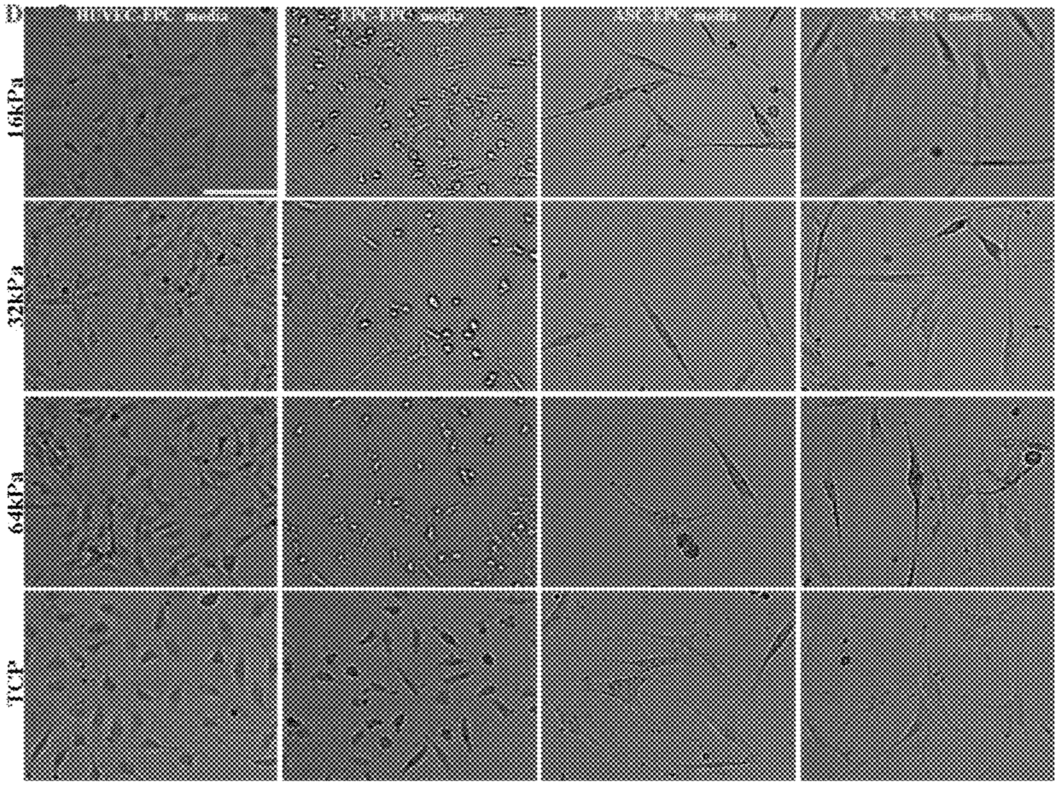

[FIG. 11C]
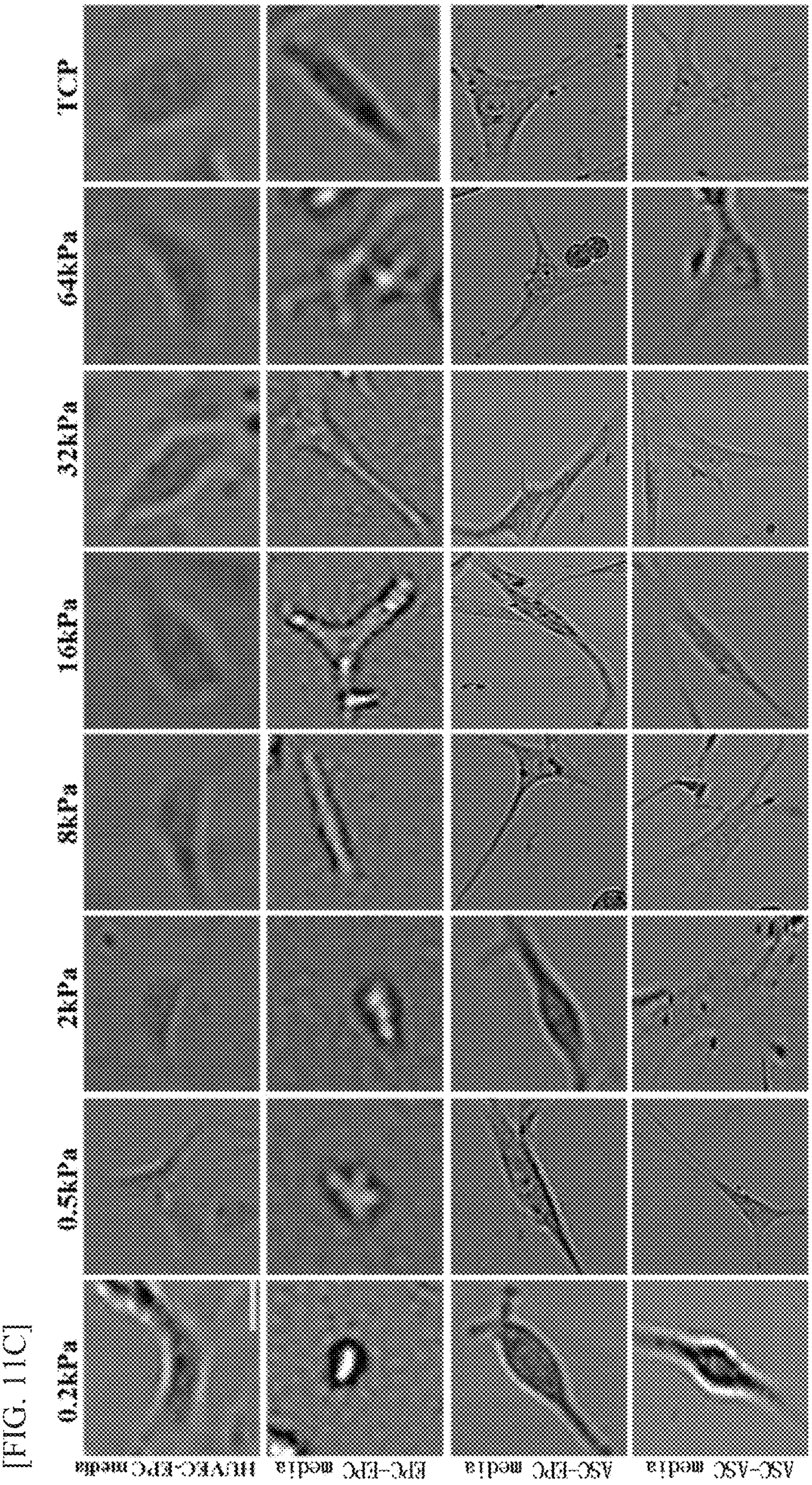

[FIG. 12A]
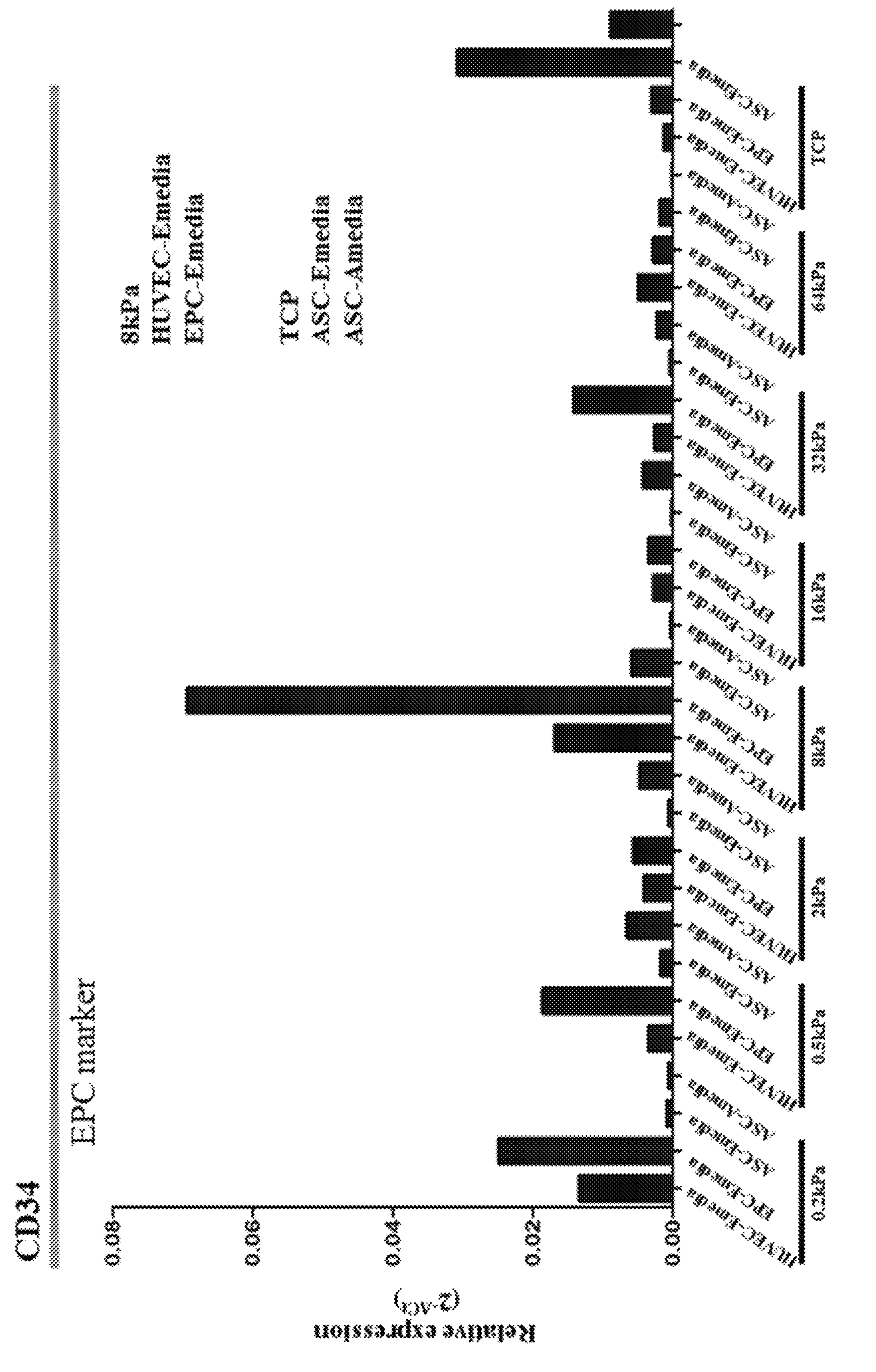

[FIG. 12B]
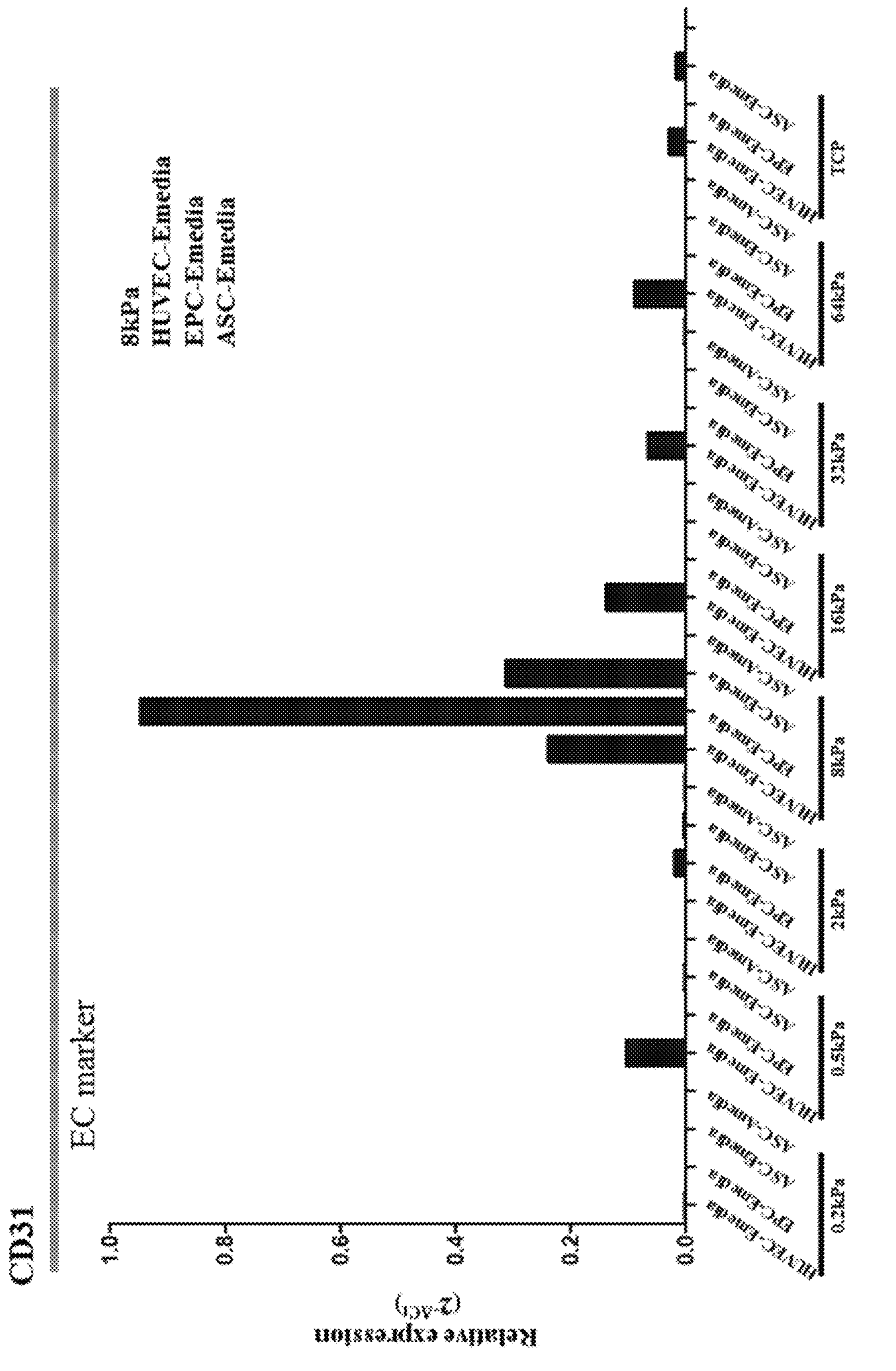

[FIG. 13A]

Preparation of Polyacrylamide hydrogel substrate
(Spin coating)

| SN | Working | | Stock | | 1X PBS ul | Total ul | APS ul | TEMED ul |
|---|---|---|---|---|---|---|---|---|
| | Acrylamide % | Bisacrylamide % | Acrylamide from 40% stock solution (ul) | Bisacrylamide from 2% stock solution (ul) | | | | |
| 1 | 8 | 0.01 | 100 | 2.5 | 397.5 | 500 | 5 | 0.5 |
| 2 | 8 | 0.04 | 100 | 10 | 390 | 500 | 5 | 0.5 |
| 3 | 8 | 0.06 | 100 | 15 | 385 | 500 | 5 | 0.5 |
| 4 | 8 | 0.08 | 100 | 20 | 380 | 500 | 5 | 0.5 |

[FIG. 13B]

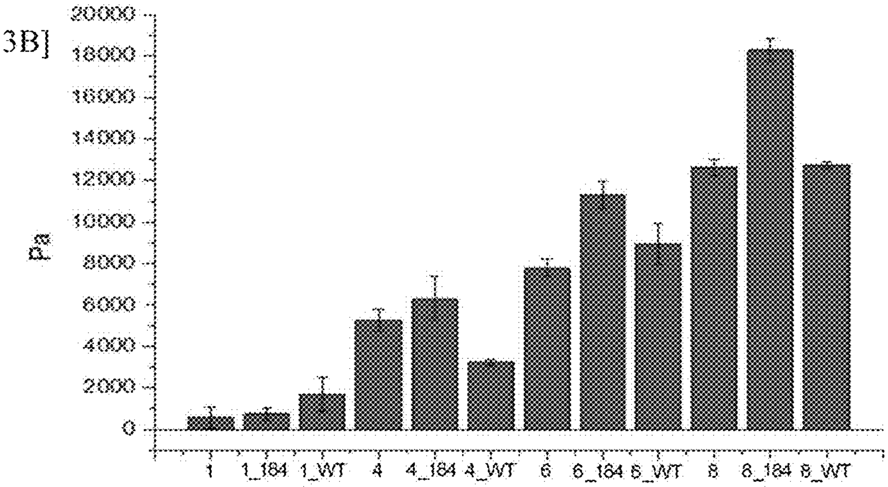

[FIG. 13C]

| SN | Working | | Stock | | Water/ Buffer ul | Total ul | APS ul | TEMED ul |
|---|---|---|---|---|---|---|---|---|
| | | | | | 10 | | | |
| | Acrylamide % | Bisacrylamide % | Acrylamide from 40% stock solution(ul) | Bisacrylamide from 2% stock solution(ul) | | | | |
| | | | 40 | 2 | | 500 | 100 | 1000 |
| 1 | 4 | 0.04 | 50 | 10 | 440 | 500 | 5 | 0.5 |
| 2 | 6 | 0.06 | 75 | 15 | 410 | 500 | 5 | 0.5 |
| 3 | 8 | 0.08 | 100 | 20 | 380 | 500 | 5 | 0.5 |
| 4 | 10 | 0.1 | 125 | 25 | 350 | 500 | 5 | 0.5 |

[FIG. 13D]

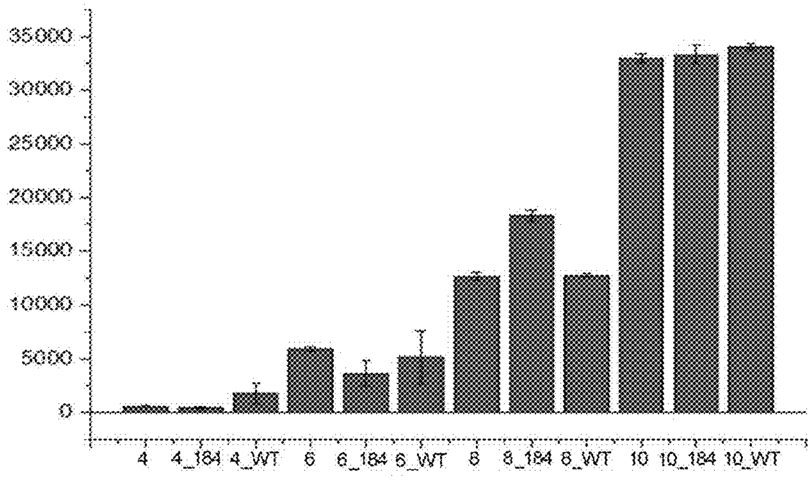

[FIG. 14]
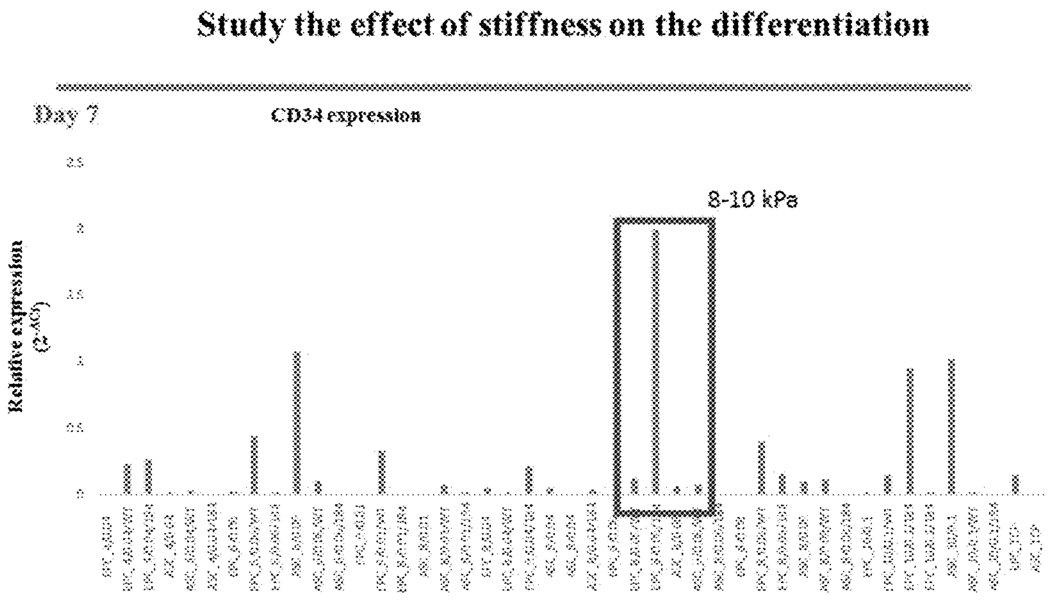

PHAGE-BASED MATRIX FOR INDUCING STEM CELL DIFFERENTIATION AND METHOD FOR PREPARING THE SAME

CROSS-REFERENCE TO RELATED APPLICATIONS

Pursuant to 35 U.S.C. § 119(e), this application claims priority to the filing date of U.S. Provisional Patent Application Ser. No. 62/556,040 filed Sep. 8, 2017, and Korean Patent Application No. 10-2017-0082035 filed Jun. 28, 2017, with the Korean Intellectual Property Office; the disclosures of which applications are incorporated herein by reference.

TECHNICAL FIELD

The present disclosure relates to a phage-based matrix for inducing stem cell differentiation and a method for preparing the same.

BACKGROUND

Conventional methods for regenerating specific cells include methods such as administration of stem cells alone or growth factors, but there are functional limitations in actually proliferating and differentiating target cells. When stem cells are used alone, the rates of engraftment and survival of the administered stem cells are low and there is a limit in controlling the proliferation and differentiation even if the stem cells are alive. As the single administration of growth factors provides only a single effect, there is a limit in exhibiting sustained effects.

Recently, according to the study results from tissue regeneration and tissue engineering fields, an importance of the cellular microenvironment, i.e., "niche," which corresponds to the external environment in which cells can regulate proliferation and differentiation is understood to be important to construct a simulated environment with biochemical and structural characteristics that can simulate the external niche.

In order to effectively achieve the intracellular environment, there are various techniques for searching for protein-protein interaction. Among them, phage display is a technique of discovering unknown amino acid sequences, which have the ability to bind to specific proteins, using recombinant bacteriophages produced by artificially introduced genes, which produce various amino acid sequences, into the genes of bacteriophages parasitic on bacteria. This technique is used in various applications, including epitope mapping, vaccine development, ligand-receptor affinity research, and bioactive peptide selecting (Smith G P, Scott J K. Libraries of peptides and proteins displayed on filamentous phage. Methods Enzymol. 279:377-380. 1993).

The representative M13 phage display system is designed to select phages, which have a strong ability to a specific protein, by a series of processes, including biopanning, using bacteriophages which express different peptides and are obtained by artificially inserting gene sequences into the ends of coat protein-producing genes of the bacteriophage genome so as to express peptides having 7-15 random amino acids and transfecting the bacteriophages into *E. coli*. When genomic DNA is artificially extracted from the selected bacteriophages and the nucleotide sequence of the artificially inserted DNA expressing specific peptides is analyzed, the desired functional peptide can be obtained.

On the other hand, it is known that specific biochemical cues in tissue ECMs play a critical role. However, the influence on the stem cells by role of physical cues such as stiffness has not been well studied.

Therefore, in a phage display, a specific coat protein is expressed on the phage surface using the phage genetic information and a polymer is used as an intermediate substance binding to the coat protein on the phage surface, thereby a nanofibrous structure of a specific strength generates through interaction between them, it can be used as a tissue matrix platform capable of inducing and regulating differentiation and proliferation of stem cells into specific cells.

SUMMARY

The present inventor has made various efforts to develop a phage-mediated structure that regulates stiffness for application to a tissue matrix platform that provides differentiation and proliferation of stem cells into specific cells, as a variety of ritual tissue engineering materials. As a result, there was developed a novel M13 phage expressing a peptide capable of crosslinking with a specific polymer on the surface and a cell delivery signal peptide was developed by a recombinant gene engineering technique using structural characteristics of a non-toxic M13 phage in human tissues. The stiffness of the nanofibrous phage-based matrix structure including the phage is controlled through the complex formation of a polymer crosslinked with the peptide displayed on the phage surface, whereby it has been confirmed that the effect of inducing differentiation of stem cells into target cells is excellent. Thereby, the present inventors completed the present disclosure.

Accordingly, it is an object of the present disclosure to provide a composition for inducing stem cell differentiation including a phage-based matrix in which a gradient of stiffness is controlled.

Another object of the present disclosure is to provide a method for preparing a phage-based matrix for inducing stem cell differentiation.

Hereinafter, the present disclosure will be described in more detail.

According to one aspect of the present disclosure, there is provided a composition for inducing stem cell differentiation including a phage-based matrix in which a gradient of stiffness is controlled by crosslinking a recombinant phage with a polymer, in which the recombinant phage displays a cell delivery peptide on major coat protein and displays HPQ on minor coat protein.

In addition, according to another aspect of the present disclosure, there is also provided a method of preparing a phage-based matrix for inducing stem cell differentiation including the following steps of:

(a) preparing a recombinant phage displaying a cell delivery peptide on major coat protein and displaying HPQ on minor coat protein;

(b) crosslinking the recombinant phage of step (a) and the polymer to generate a phage-based matrix that gradient of stiffness is controlled; and (c) culturing stem cells in the phage-based matrix of step (b) to induce differentiation into target cells.

As used herein, the term "matrix" is understood to mean a tissue engineering material capable of providing a biomimetic 2D or 3D microenvironment suitable for cell culture or differentiation, and in the present disclosure, means a recombinant pulling matrix (Phage based pulling patterned patch; PhaTch) or a recombinant phage gel system (Phage based hydro gel; PhaGel) as a matrix immobilized by crosslinking a recombinant phase with a polymer substance.

As used herein, the term "peptide" refers to a linear molecule formed by binding amino acid residues together by peptide bonds.

As used herein, the term "cell delivery peptide" is used interchangeably with "signal peptide" and "signal sequence," and corresponds to a cell adhesion motif. Accordingly, a longer amino acid sequence including a cell adhesion amino acid sequence as an essential sequence is also included in the scope of the present disclosure.

According to a preferred embodiment of the present disclosure, the cell delivery peptide, which is a cell adhesion amino acid sequence, contained in the peptide of the present disclosure is selected from the group consisting of RGD (Arg-Gly-Asp), RGDS (Arg-Gly-Asp-Ser), RGDC (Arg-Gly-Asp-Cys), RGDV (Arg-Gly-Asp-Val), RGES (Arg-Gly-Glu-Ser), RGDSPASSKP (Arg-Gly-Asp-Ser-Pro-Ala-Ser-Ser-Lys-Pro), GRGDS (Gly-Arg-Gly-Asp-Ser), GRADSP (Gly-Arg-Ala-Asp-Ser-Pro), KGDS (Lys-Gly-Asp-Ser), GRGDSP (Gly-Arg-Gly-Asp-Ser-Pro), GRGDTP (Gly-Arg-Gly-Asp-Thr-Pro), GRGES (Gly-Arg-Gly-Glu-Ser), GRGDSPC (Gly-Arg-Gly-Asp-Ser-Pro-Cys), GRGESP (Gly-Arg-Gly-Glu-Ser-Pro), SDGR (Ser-Asp-Gly-Arg), YRGDS (Tyr-Arg-Gly-Asp-Ser), GQQHHLGGAKQAGDV (Gly-Gln-Gln-His-His-Leu-Gly-Gly-Ala-Lys-Gln-Ala-Gly-Asp-Val), GPR (Gly-Pro-Arg), GHK (Gly-His-Lys), YIGSR (Tyr-Ile-Gly-Ser-Arg), PDSGR (Pro-Asp-Ser-Gly-Arg), CDPGYIGSR (Cys-Asp-Pro-Gly-Tyr-Ile-Gly-Ser-Arg), LCFR (Leu-Cys-Phe-Arg), EIL (Glu-Ile-Leu), EILDV (Glu-Ile-Leu-Asp-Val), EILDVPST (Glu-Ile-Leu-Asp-Val-Pro-Ser-Thr), EILEVPST (Glu-Ile-Leu-Glu-Val-Pro-Ser-Thr), LDV (Leu-Asp-Val), and LDVPS (Leu-Asp-Val-Pro-Ser), more preferably, selected from the group selected from RGD (Arg-Gly-Asp), RGDS (Arg-Gly-Asp-Ser), RGDC (Arg-Gly-Asp-Cys), RGDV (Arg-Gly-Asp-Val), and RGES (Arg-Gly-Glu-Ser), and most preferably, RGD (Arg-Gly-Asp).

The term "Arg-Gly-Asp peptide" or "RGD peptide" refers to an "Arg-Gly-Asp group of receptors"; for example, a peptide having one or more of Arg-Gly-Asp containing a sequence which can function as a binding site for the receptor of integrin. RGD peptides also include peptides with amino acids that are functional equivalents of RGD peptides when interacting with the same RGD receptor.

Preferably, the recombinant phage of the present disclosure includes a GRGDSDDY peptide in a P8 peel protein.

Peptides containing the HPQ or RGD sequences of the present disclosure can be synthesized from amino acids by means well known in the pertinent art.

As used herein, the term "phage" or "bacteriophage" is a type of virus that infects bacteria and is often abbreviated as phage. A phage is a simple structural organism in which the core of a genetic material composed of a nucleic acid is covered by a protein coat, and the nucleic acid is a single chain or a double-stranded DNA or RNA. This nucleic acid is a simple structure covered by a protein coat. It is divided into three basic structures: A form with a tail on an icosahedral head, a form without a tail on an icosahedral head, and a filament form. The most common form of bacteriophage with tail on icosahedral head is Myoviridae with a shrinkable tail, Siphoviridae with a long non-shrinkable tail, and Podoviridae with a short tail, according to the characteristics of a tail. The bacteriophages without tail on icosahedral head are subdivided according to the shape of head, the constituent of head, and the presence or absence of coat. Finally, bacteriophages in the form of filaments are subdivided by size, shape, coat, and filament constituents (H. W. Ackermann, Frequency of morphological phage descriptions in the year 2000; Arch. Virol. 146: 843-857, 2001; Elizabeth Kutter, et al., Bacteriophages Biology and Application, CRC press).

The phage is not limited in its kind and may be T1, T2, T4, T6 or lambda, mu, M13, and the like. In the present disclosure, M13 is used.

The recombinant phage of the present disclosure artificially inserts a gene sequence to express a desired peptide having 3 to 15 amino acid sequences in a gene that produces a coat protein in the genome of the M13 phage and expresses the desired peptide.

The phage is composed of various coat proteins and may be composed of, for example, P3 (PIII), P6 (PVI), P7 (VII), P8 (VIII), P9 (IX), and the like.

According to a preferred embodiment of the present disclosure, the coat protein is at least one selected from the group consisting of P3, P6, P7, P8, and P9.

In the present disclosure, the recombinant phage of the present disclosure includes a peptide in at least one selected from the group consisting of P3, P8, and P9, more preferably the peptide may be contained in the P3 or P8 protein.

Preferably, the desired peptide is an HPQ peptide and a cell delivery peptide.

In addition, the bacteriophage of the present disclosure includes an HPQ peptide in at least one protein selected from the group consisting of P3, P7 and P9, which are minor coat proteins, and more preferably an HPQ peptide may be included in P3, P7 and P9 proteins.

In the present disclosure, the recombinant phage of the present disclosure may include a cell delivery peptide consisting of 5 to 10 amino acid sequences including an RGD peptide as a cell delivery peptide in P8, which is a major coat protein, and most preferably including RGD.

That is, the recombinant phage of the present disclosure is (i) a recombinant M13 phage (p7HPQp8RGDp3HPQ) in which RGD having cell affinity is expressed in P8, which is the major coat protein, and various growth factors and cytokines are fixed via the medium of a polymer, or P3 and P7, which are minor coat proteins that can be used for stiffness achievement; and (ii) a recombinant M13 phage (p9HPQp8RGDp3HPQ) in which RGD having cell affinity is expressed in P8, which is the major coat protein, and various growth factors and cytokines are fixed via the medium of a polymer, or P3 and P9, which are minor coat proteins that can be used for stiffness achievement.

Preferably, the recombinant M13 phage (represented by p7HPQp8RGDp3HPQ or recombinant phage YSY 184) includes a genome consisting of the nucleotide sequence represented by SEQ ID NO: 2, and the recombinant M13 phage (represented by p9HPQp8RGDp3HPQ or recombinant phage YSY165) includes a genome consisting of the nucleotide sequence represented by SEQ ID NO: 3.

The genetically engineered phage can develop other combinations based on the specific use by a person skilled in the art. Methods can be developed to display peptides on some or substantially all copies of the coat protein.

In the present disclosure, any kind of polymer may be used as long as the polymer can form a stiffness gradient by crosslinking with the phage of the present disclosure.

For example, it may be at least one selected from the group consisting of streptavidin, PDDA (poly(diallyldimethylammonium chloride), polyacrylamide, and bisacrylamide, but is not limited thereto.

In addition, according to a preferred embodiment of the present disclosure, the present method increases the stiffness of the phage-based matrix as the concentration of streptavidin, polyacrylamide, or bisacrylamide increases, and as the concentration of PDDA increases, the stiffness of the phage-based matrix decreases so that the stiffness gradient can be formed.

Preferably, the stiffness formed by the recombinant phage-based matrix of the present disclosure is from 1 kPa to 1 MPa, more preferably from 1 to 500 kPa, even more preferably from 1 to 100 kPa, and the optimum stiffness may be adjusted depending on the target cells.

In addition, according to a preferred embodiment of the present disclosure, the recombinant phage of the present disclosure excellently induces differentiation of stem cells into target cells.

Preferably, the stem cells are selected from the group consisting of MSC (Mesenchymal Stem Cells), ASC (Adipose Stem Cell), EPCs (Endothelial Progenitor Cells), CPC (cardiac progenitor cell), ECFCs (Endothelial Colony Forming Cells), VPCs (Vasculogenic Progenitor Cells), and Embryonic Stem Cells.

As used herein, the term "culturing" used in referring to the differentiation of stem cells into target cells can be carried out using a differentiation culture method known in the pertinent art as long as it can attain the aimed differentiation. In one embodiment of the present disclosure, a medium differentiation method was used, but is not limited thereto.

As used herein, the term "media" means a medium that enables stem cell growth, differentiation and survival in vitro, and includes all the conventional media used in the pertinent art suitable for culturing stem cells. Depending on the type of cells, medium and culture conditions may be selected. The medium used for the culture is preferably a cell culture minimum medium (CCMM), and generally includes a carbon source, a nitrogen source and a trace element component. For example, the examples of such cell culture minimum medium include DMEM (Dulbecco's Modified Eagle's Medium), MEM (Minimal essential Medium), BME (Basal Medium Eagle), RPMI1640, F-10, F-12, αMEM (α Minimal essential Medium), GMEM (Glasgow's Minimal essential Medium), Iscove's Modified Dulbecco's Medium, and the like, but are not limited thereto.

The medium may also include antibiotics such as penicillin, streptomycin, gentamicin, and the like.

The composition of the present disclosure may further include a crosslinking agent and a natural polymer The crosslinking agent includes at least one selected from the group consisting of glutaraldehyde, Genipin and carbodiimide, more preferably glutaraldehyde or Genipin, and most preferably glutaraldehyde.

The natural polymer includes at least one selected from the group consisting of collagen, denatured collagen, alginate, denatured alginate, hyaluronic acid, denatured hyaluronic acid, gelatin, denatured gelatin, chitosan, denatured chitosan, fibrin, and denatured fibrin, but is not limited thereto.

The crosslinking agent and the natural polymer may be mixed and crosslinked or individually treated separately. That is, the crosslinking agent and the natural polymer may be mixed and crosslinked at a weight ratio of 1:1 to 100, or the crosslinking agent and the natural polymer may be individually treated at a weight ratio of 1:1 to 100, preferably individually treated at a weight ratio of 1:1.

In the present disclosure, the stiffness capable of promoting differentiation from stem cells into soft tissues is preferably 1 to 20 kPa, more preferably 1 to 15 kPa, even more preferably 5 to 10 kPa, and most preferably, 8 to 10 kPa.

The soft tissue is preferably selected from the group consisting of vascular cells (vascular endothelial cells), muscle cells and cardiac cells, and most preferably vascular cells.

In the present disclosure, the stiffness capable of promoting differentiation from stem cells into hard tissues is preferably 1 to 1000 kPa, more preferably 20 to 500 kPa, even more preferably 40 to 200 kPa, even further more preferably 60 to 100 kPa, and most preferably 80 to 90 kPa.

The hard tissue is preferably a bone cell, such as a bone cell or a dental cell.

In the present disclosure, the stiffness is a value measured in a solution state similar to a solution in the body, for example, physiological saline or PBS.

Therefore, the present disclosure uses the genetic information of a phage to produce a specific coat protein on the phage surface, and uses the binding of a specific substance to the coat protein of the phage surface to control the stiffness of a phage-matrix, thereby providing physical and mechanical niche environment created by the formation of a nanofibrous structure of the phage to promote differentiation.

The method of the present disclosure provides a physical and mechanical niche environment created by the formation of a nanofibrous structure of the phage whose stiffness is controlled, thereby promoting the differentiation of stem cells into target cells. Therefore, it can be applied to a tissue matrix platform as a variety of conventional tissue engineering materials.

BRIEF DESCRIPTION OF THE DRAWINGS

FIG. 1A illustrates a cleavage map of recombinant M13. FIG. 1B illustrates the results of sequencing of a phage (p7HPQp8RGDp3HPQ) containing RGD in the major coat p8 region of the phage and expressing HPQ in the minor coat p3 and p7 regions. FIG. 1C illustrates the results of sequencing of a phage (p9HPQp8RGDp3HPQ) containing RGD in the major coat p8 region of the phage and expressing HPQ in the minor coat p3 and p9 regions.

FIG. 2 schematically illustrates a process of forming a stiffness-graded phage matrix according to recombination phage pulling (patterning).

FIG. 3 illustrates the difference in cell response due to interaction with a recombinant phage in recombinant phage pulling (patterning).

FIG. 4 illustrates the difference in cell differentiation due to interaction with a recombinant phage in recombinant phage pulling (patterning).

FIG. 5 illustrates the results of osteogenic differentiation of cells by recombinant phage-based matrix (PhaTch) in recombinant phage pulling (patterning).

FIG. 6 illustrates AFM (atomic force microscopy) results obtained by pulling the modified M13 phage on a gold panel.

FIGS. 7A-7B illustrate the results of induction of differentiation (bone formation) of stem cells into bone cells according to the stiffness of a recombinant phage pulling matrix.

FIG. 8 schematically illustrates stiffness-graded phage matrix formation process according to a recombinant phage gel system (PhaGel).

FIG. 9 illustrates the difference in cell response due to interaction with a recombinant phage in a recombinant phage gel system (PhaGel).

FIG. 10 illustrates the results of induction of differentiation (angiogenesis) of stem cells into vascular cells according to the stiffness of a recombinant phage gel matrix.

FIGS. 11A-11C illustrate the morphology of cells on day 2 in a recombinant phage gel matrix.

FIGS. 12A-12B illustrate the expression levels of CD34, the EPC marker and CD31, the EC marker on day 2 in a recombinant phage gel matrix.

FIGS. 13A-13D illustrate the stiffness according to a recombinant phage gel matrix prepared at various concentrations.

FIG. 14 illustrates the expression level of CD34, the EPC marker on day 7, when stem cells were differentiated in recombinant phage gel matrices having different stiffness.

DETAILED DESCRIPTION

Hereinafter, it will be apparent to a person having ordinary skill in the technical field to which the present disclosure pertains that the examples are for illustrative purposes only in more details and that the scope of the present disclosure is not construed as being limited by these examples without departing from gist of the present disclosure.

Example 1. Preparation of Novel Recombinant Phage

For the preparation of functional M13 phage that can control stiffness for application to tissue matrix platforms that provide differentiation and proliferation of stem cells into specific cells, the present inventors prepared and constructed M13 phages p7HPQp8RGDp3HPQ (SEQ ID NO: 2) and p9HPQp8RGDp3HPQ (SEQ ID NO: 3), which expresse RGD having cell affinity on their p8 major coat protein, and express HPQ which can be used for fixing various growth factors and cytokines with a medium of streptavidin or implementing stiffness, on p3, p7, and/or p9 minor coat proteins.

The structure of the newly constructed M13 phage (FIG. 1A) and the sequencing confirmation result thereof (FIG. 1B) are shown in FIG. 1.

In addition, the types of phage constructed are shown in Table 1, and the primer sequences used for phage construction are shown in Table 2.

TABLE 1

| Name | p7 Sequence | p9 sequence | p8 sequence | p3 sequence | comments |
|---|---|---|---|---|---|
| RDD8H3H9 | MEQV | TSHPQS* | AGGRGD SDDYDP | SHSACHPQGPLC GGGAET | C-terminus HPQ engineering on p9 |
| RDD8H3HX9 | MEQV | TSA(Q)H PQHRS* | AGGRGD SDDYDP | SHSACHPQGPLC GGGAET | C-terminus HPQ engineering on p9 |
| RDGDY8H3HX9 | MEQV | TSA(Q)H PQHRS* | AGGRGD SDDYDP | SHSACHPQGPLC GGGAET | C-terminus HPQ engineering on p9 |
| RDGDY8H3HX9 | MEQV | TSA(Q)H PQHRS* | AGGRGD SDDYDP | SHSACHPQGPLC GGGAET | C-terminus HPQ engineering on p9 |
| RGD8HPQ3HPQ9 | MEQV | TSHPQS* | ADLGRG DTEDP | SHSACHPQGPLC GGGAET | C-terminus HPQ engineering on p9 |
| RGD8HLQ3HPQ9 | MEQV | TSHPQS* | ADLGRG DTEDP | SHSACHLQGPLC GGGAET | C-terminus HPQ engineering on p9, HPQ on p3 mutated |
| RGE8HPQ3HPQ9 | MEQV | TSPQHP QNKS* | ADSGRG ETEDP | SHSACHPQGPLC GGGAET | C-terminus HPQ engineering on p9 |
| RD8H3H7 | ME-HPQ-V | MSV | AGGRGD SDGYDP | SHSACHPQGPLC GGGAET | N-terminus HPQ engineering on p7 |
| RD8H3H9 | QRDP* | MSHPQV | AGGRGD SDGYDP | SHSACHPQGPLC GGGAET | N-terminus HPQ engineering on p9, c-teminus of p7 will be changed |
| RD8H3cH7-1 | MECLHP QTCV | MSV | AGGRGD SDGYDP | SHSACHPQGPLC GGGAET | N-terminus circular HPQ engineering on p7 |
| RD8H3cH7-2 | MECWH PQMCV | MSV | AGGRGD SDGYDP | SHSACHPQGPLC GGGAET | N-terminus circular HPQ engineering on p7 |

TABLE 2

| | |
|---|---|
| p8-RDDD Fw | 5'-ATATATCTGCAGNNGGCCGTGGCGATTCTGATGACGATGATCCCGCAAAAGCGGCCTTTAATCCC-3' (SEQ ID: 4) |
| p8-rev1376 (rev1376) | 5'-CCTCTGCAGCGAAAGACAGCATCGG-3' (SEQ ID: 5) |
| p3-Fwd1626 | 5'-AAACACT CGGCCG AAACTGTTGAAAGT TGTTTAGC-3' (SEQ ID: 6) |
| p3-rev RGD | 5'-TATATA CGGCCG A TCCACCGCCGCAGC TATCGCCACGGCCGCACGC CGAGTGAGAATAGAAAGGAACCACTAAAG GAATTGCG-3' (SEQ ID: 7) |
| Fw-BspHI-p9 | 5'-AAACAC TCATGA AAA AGT CTT TAG TCC TCA AAG CCT CTG TAG-3' (SEQ ID: 8) |
| Re-BspHI-HPQ-p9 | 5'-TATATATCATGANTCAGCTCTGCGGATGGGAAG TTTCCATTAAACG-3' (SEQ ID: 9) |
| Re-BspHI-XXHPQXXS-p9 | 5'-TATATATCATGANTCAGCTMNNMNNCTGCGGATGMNNMNNGGAAGTTTCCATTAACG-3' (SEQ ID: 10) |
| BamHI-N-HPQ Fw p7 | 5'-ATATATGGATCCATGGAGCATCCGCAGGTCGCGGATTTCGACACAATTTATCAG-3' (SEQ ID: 11) |
| BamHI-N-HPQ Re p7 | 5'-AAACACGGATCCGTTACTTAGCCGGAACGAGGCGCAGACGGT-3' (SEQ ID: 12) |

TABLE 2-continued

| | |
|---|---|
| BamHI-N-HPQ Fw p9 | 5'-ATATATGGATCCATGAGTCATCCGCAGGTTTTAGTGTATTCTTTTGCCTCTTTCGTT-3' (SEQ ID: 13) |
| BamHI-N-HPQ Re p9 | 5'-AAACACGGATCCCTTTGACCCCCAGCGATTATACCAAGCGC-3' (SEQ ID: 14) |
| BamHI-cir N-HPQ Fw p7 | 5'-ATATATGGATCCATGGAGTGCNNKCATCCGCAGNNKTGTGTCGCGGATTTCGACACAATTTATCAG-3' (SEQ ID: 15) |
| BamHI-cir N-HPQ Fw p9 | 5'-ATATATGGATCCATGAGTTGCNNKCATCCGCAGNNKTGTGTTTTAGTGTATTCTTTTGCCTCTTTCGTT-3' (SEQ ID: 16) |

More specifically, as wild-type phage M13WT (SEQ ID NO: 1), M13KE (New England Biolabs, Ipswich, Mass.; N0316S) was purchased to use. The phage M13s (SEQ ID NOS: 2 and 3) having the vector map of FIG. 1A used in the present disclosure were produced by a gene recombinant technique known in the pertinent art.

Example 2: Achievement of a Phage Matrix with Different Stiffness Regulated by a Novel Recombinant Phage and Induction Effect on Stem Cell Differentiation Thereby The present inventors formed the phage matrix, which is a nanofibrous structure, using the phage constructed in Example 1, and confirmed the reaction and differentiation of cells by controlling the stiffness thereof.

2-1. Phage Engineering and Formation of Phage Matrix by Pulling (Patterning)

In order to form a phage matrix (Phage based pulling patterned patch: PhaTch) by pulling (patterning) the phage expressing the RGD-peptide and HPQ-peptide of the present disclosure constructed in Example 1 above, the present inventors combined streptavidin or PDDA with a recombinant phage (FIG. 2).

First, a hydrophilic treatment was performed on a glass slide glass, and then the prepared phage matrix was adhered.

The phage matrix was crosslinked with glutaraldehyde vapor.

When osteocytes were cultured on glass slide glass coated with phage matrices ($10^{12}$ phages/mL) expressing DGEA, DGDA, EGEA, RGD, RGE peptides (DGEA is used as a collagen functional peptide. DGDA and EGEA are used as comparative peptides to identify DGEA-specific functions by substituting amino acids (D and E) having a similar property to DGEA. RGD is a fibronectin and ECM-like functional peptide and is used as a cell-affinity peptide. RGE is used as a comparative peptide to identify RGD-specific functions by substituting amino acids (D and E) having a similar property to RGD), the difference in the reaction of the osteocytes by the interaction with the recombinant phage was confirmed.

As a result, as shown in FIG. 3, it can be seen that osteoblasts respond very specifically to DGEA. When osteoblasts were cultured on a DGEA phage, the area of osteoblasts was larger in DGEA than in the other peptide expression phages.

In addition, the difference in cell differentiation due to interaction with the recombinant phage was confirmed.

As a result, as shown in FIG. 4, it can be seen that the ALP activation reaction on the DGEA phage is high. This indicates that the degree of differentiation is different due to the interaction with the peptide expressed on the DGEA phage.

In addition, as shown in FIG. 5, the expressions of bone cell differentiation markers (COL1, OP, ALP, OCN and Dmp1) are highly expressed in osteoblasts cultured on a DGEA phage. It can be also seen that the interaction of peptides expressed on the DEGA phage makes the cells react, and that these interactions influence the differentiation. As such, DGEA is an osteogenic specific peptide, so that a specific reaction of osteoblasts can be observed.

As such, it was found that the reaction and differentiation of cells can be controlled depending on the peptides displayed in recombinant phages.

On the other hand, modified M13 phage, streptavidin and PDDA were pulled on a gold panel and images were confirmed for the achievement of a matrix suitable for cell culture with various stiffness prepared using streptavidin and PDDA (FIG. 6, top panel)

As a result, as shown in FIG. 6, the thickness of the implemented matrix was not related to the stiffness (FIG. 6, lower left panel), and the difference in stiffness with or without PDDA or streptavidin was clearly noted (FIG. 6, lower right panel).

Accordingly, the RGD-peptide and the HPQ-peptide of the nanofiber were mixed with streptavidin or PDDA to control the stiffness of the phage matrix using a recombinant phage, and the stiffness was controlled based on the concentration of the phage and the mixing substance. That is, the stiffness can be controlled according to the concentrations of phage, streptavidin and PDDA, or according to the matrix achievement methods (pulling order, pulling rate, mixing ratio and method with streptavidin and PDDA, etc.). The stiffness of 20 to 120 kPa, the averagely high stiffness of 120 to 2900 kPa of the phage pulled by using streptavidin, and the low stiffness of 8 to 20 kPa of the phage pulled by using PDDA can be implemented by the concentration of the phage, etc.

2-2. Induction of Differentiation of Stem Cells into Osteoblasts (Osteogenesis) According to Phage Matrix Stiffness The present inventors evaluated morphological changes and gene expression during bone differentiation in vitro by controlling the stiffness of the constructed phage matrix to various sizes.

As a result, as shown in FIG. 7A, it can be understood that the stiffness can be controlled according to a ratio and a way of pulling.

In addition, as shown in FIG. 7B, the higher the stiffness was, the higher the expression of osteogenic marker was observed, which proved to induce bone differentiation.

Example 3: Achievement of a Phage Gel System (PhaGel) with a Controlled Stiffness Using a Novel Recombinant Phage and its Induction Effect on Stem Cell Differentiation The present inventors formed a phage gel, which is composed of the nanofibrous structured phage constructed in Example 1, and confirmed the reaction and differentiation of cells by controlling the stiffness thereof.

3-1. Phage Engineering and Formation of Phage Matrices According to a Gel System (PhaGel)

The present inventors formed a phage matrix (Phage based hydrogel: PhaGel) by combining the phage with the RGD-peptide and HPQ-peptide of the present disclosure constructed in Example 1 with the gel system, and in order to control the stiffness, constructed the PhaGel system by mixing polyacrylamide and bisacrylamide at various ratios together with the recombinant phage (FIG. 8).

First, a hydrophilic treatment was performed on a glass slide glass, and then the prepared phage hydrogel was attached.

ASC (Adipose Stem Cell; ATCC, PCS-500-011) was cultured on a glass slide glass coated with the PhaGel. On an ASC medium, for differentiation into each differentiation medium (for differentiation into vascular endothelial cells, a vascular endothelial cell differentiation medium was used, and for differentiation into osteoblasts, an osteoblast differentiation medium was used) vascular endothelial cell, a medium containing VEGF and/or IGF can be used. In this experiment, Endothelial basal medium-2 (LONZA, USA) supplemented with EGM™-2MV SingleQuots™ kit (E-media, LONZA, USA) was used. ASC medium (ATCC® PCS-500-030™) may be used for comparison. The difference in cell response due to the interaction with a recombinant phage was confirmed.

As a result, as shown in FIG. 9, as the content of bisacrylamide increased, the stiffness became stronger (FIG. 9, left panel). On the $7^{th}$ day of culture, ASC cultured in PhaGel was attached, whereas ASC cultured in hydrogel, which is a control group, was not attached (FIG. 9, middle panel). In addition, there was a significant difference in the aspect ratios between all the experimental groups at each time point (FIG. 9. upper right panel), and ASCs cultured in PhaGel showed significantly increased cell area on the $7^{th}$ day of culture (FIG. 9, lower right panel).

That is, the control of the stiffness can be controlled by the mixing ratio of polyacrylamide and bisacrylamide. The present inventors observed that the stiffness was significantly changed when the wild-type phage or the recombinant phage was mixed, and that the cells were grown only in the gel mixed with the phage.

3-2. Induction of Differentiation (Vascularization) of Stem Cells into Vascular Cells According to Stiffness of Phage Gel (PhaGel)

The present inventors adjusted the stiffness of the constructed PhaGel in various sizes to evaluate morphological changes and gene expression during angiogenesis differentiation in vitro and in vivo.

As a result, as shown in FIG. 10, it can be understood that when ASCs at 2 kPa and 16 kPa were grown in an EPC medium and an ASC medium, more angiogenic markers were expressed at 16 kPa than 2 kPa when grown on an EPC medium. On the other hand, there was no expression of angiogenic markers on an ASC medium. In other words, it was found that the environment inducing the differentiation of vascular endothelial cells was established at 16 kPa rather than 2 kPa.

In addition, as shown in FIGS. 11A-11C, the morphology of the cells was confirmed on day 2.

In the undifferentiated EPC and ASC cultures, round-shaped cells were observed up to 0.2 to 2 kPa, and the changes from a round-shape to an elongated shape at 8 to 16 kPa, and relatively high cell affinity (cell distribution and number) were observed. Therefrom, it is expected that the induction of differentiation such as adipogenic cells (adipocytes) will be advantageous at 2 kPa or less, and for affinity and differentiation of vascular endothelial cells, it will be advantageous at about 8 to 16 kPa.

In addition, the expressions of EPC marker CD34 and EC marker CD31 were confirmed at day 2.

As a result, as shown in FIGS. 12A and 12B, it was found that the differentiation toward EC was promoted around 8 kPa.

Further, as shown in FIG. 13, when wild type phage (WT) or recombinant phage 184 (YSY184; hereinafter referred to as "184") according to the mixing ratio (FIGS. 13A and 13C) of acrylamide and bisacrylamide for producing a polyacrylamide hydrogel substrate was added, it was confirmed that the stiffness was significantly changed (FIGS. 13B and 13D). For example, when the acrylamide is 8% and the bisacrylamide is 0.06%, the stiffness is 8 to 10 kPa when the recombinant phage (denoted as 6_184 in FIG. 13B) and the wild type phage (denoted as 6_WT in FIG. 13B) were added. On the other hand, the stiffness was 5 kPa or less when the recombinant phage (denoted as 6_184 in FIG. 13D) and the wild type phage (denoted as 6_WT in FIG. 13D) were added if the acrylamide was 6% and the bisacrylamide was 0.06%.

In addition, when the recombinant phage (184) or the wild type phage (WT) was added to the above-mentioned various concentrations of gel, the expression level of CD34 was confirmed when the EPC and ASC were cultured on the $7^{th}$ day in a gel having a stiffness with various gradients.

As a result, as shown in FIG. 14, the expression level of CD34 was the highest at a stiffness of 8 to 10 kPa. PhaGel with recombinant phage 184 contributes to the regulation of vascular differentiation, while having a stiffness of 8 to 10 kPa, whereas the hydrogel without phage but with the same stiffness does not exhibit cell-affinity and differentiation control ability. It can be seen that the proper differentiation of cells can be controlled through the interaction between the stiffness realized by the matrix using a phage and the cell affinity peptides of the constituting phage.

Accordingly, it can be seen that the above results can realize various stiffness with the Phage based Matrix (PhaTch or PhaGel) of the present disclosure, and that the addition of phage contributes to the stiffness, and in particular, when the stiffness is 8 to 10 kPa, it was confirmed that EPC and EC differentiation were optimum conditions and that the optimum condition of bone differentiation was obtained at a stiffness of 80 kPa to 90 kPa.

In conclusion, the present disclosure provides a method of regulating the degree of differentiation of stem cells by controlling the stiffness formed according to the functions of the phage, and the matrix concentration and structure.

What is claimed is:

1. A composition for inducing differentiation of stem cells into osteocytes or endothelial cells (EC), comprising a phage-based matrix in which a gradient of stiffness is controlled by crosslinking a recombinant phage with a polymer, wherein the recombinant phage is a recombinant phage displaying a cell delivery peptide on a major coat protein and displaying HPQ on a minor coat protein;

wherein the recombinant phage comprises a genome consisting of the nucleotide sequence represented by SEQ ID NO: 2 or 3;

wherein the polymer is at least one selected from the group consisting of streptavidin, poly(diallyldimethylammonium chloride) (PDDA), polyacrylamide and bisacrylamide; and wherein the stiffness generated is 1 kPa to 1 MPa 8 to 10 kPa for differentiation of the stem cells into endothelial cells or 80 kPa to 90 kPa for differentiation of the stem cells into osteocytes.

2. The composition according to claim 1, wherein the stem cell is selected from the group consisting of Mesenchymal Stein Cells (MSC), Adipose Stein Cells (ASC), Endothelial Progenitor Cells (EPC), Cardiac Progenitor Cells (CPC), Endothelial Colony Forming Cells (ECFC), Vasculogenic Progenitor Cells (VPC) and embryonic Stem Cells.

3. The composition according to claim 1, wherein the recombinant phage comprises a genome consisting of the nucleotide sequence represented by SEQ ID NO: 2.

4. The composition according to claim 1, wherein the recombinant phage comprises a genome consisting of the nucleotide sequence represented by SEQ ID NO: 3.

5. The composition according to claim 1, wherein the recombinant phage comprises a genome consisting of the nucleotide sequence represented by SEQ ID NO: 2 and wherein the stiffness generated is 8 to 10 kPa for differentiation of stem cells into endothelial cells or 80 kPa to 90 kPa for differentiation of stem cells into osteocytes.

* * * * *

UNITED STATES PATENT AND TRADEMARK OFFICE

CERTIFICATE OF CORRECTION

PATENT NO. : 10,604,737 B2
APPLICATION NO. : 15/907184
DATED : March 31, 2020
INVENTOR(S) : So Young Yoo It is certified that error appears in the above-identified patent and that said Letters Patent is hereby corrected as shown below:

In the Claims

Please replace "Mesenchymal Stein Cells (MSC), Adipose Stein Cells (ASC)" in Claim 2 with -- Mesenchymal Stem Cells (MSC), Adipose Stem Cells (ASC) -- (Column 36, Lines 65-66).

Signed and Sealed this
Twenty-sixth Day of May, 2020

Andrei Iancu
*Director of the United States Patent and Trademark Office*

SEQUENCE LISTING

<160> NUMBER OF SEQ ID NOS: 16

<210> SEQ ID NO 1
<211> LENGTH: 7222
<212> TYPE: DNA
<213> ORGANISM: bacteriophage M13 WT

<400> SEQUENCE: 1

-continued

```
aatgctacta ctattagtag aattgatgcc accttttcag ctcgcgcccc aaatgaaaat     60
atagctaaac aggttattga ccatttgcga aatgtatcta atggtcaaac taaatctact    120
cgttcgcaga attgggaatc aactgttata tggaatgaaa cttccagaca ccgtacttta    180
gttgcatatt taaaacatgt tgagctacag cattatattc agcaattaag ctctaagcca    240
tccgcaaaaa tgacctctta tcaaaaggag caattaaagg tactctctaa tcctgacctg    300
ttggagtttg cttccggtct ggttcgcttt gaagctcgaa ttaaaacgcg atatttgaag    360
tctttcgggc ttcctcttaa tctttttgat gcaatccgct ttgcttctga ctataatagt    420
cagggtaaag acctgatttt tgatttatgg tcattctcgt tttctgaact gtttaaagca    480
tttgaggggg attcaatgaa tatttatgac gattccgcag tattggacgc tatccagtct    540
aaacatttta ctattacccc ctctggcaaa acttcttttg caaaagcctc tcgctatttt    600
ggtttttatc gtcgtctggt aaacgagggt tatgatagtg ttgctcttac tatgcctcgt    660
aattcctttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt    900
ctcgtcaggg caagccttat tcactgaatg agcagctttg ttacgttgat ttgggtaatg    960
aatatccggt tcttgtcaag attactcttg atgaaggtca gccagcctat gcgcctggtc   1020
tgtacaccgt tcatctgtcc tctttcaaag ttggtcagtt cggttccctt atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctgggggt   1200
caaagatgag tgttttagtg tattcttttg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctcctttt ggagcctttt   1560
ttttggagat tttcaacgtg aaaaaattat tattcgcaat tcctttagtg gtacctttct   1620
attctcactc ggccgaaact gttgaaagtt gtttagcaaa atcccataca gaaaattcat   1680
ttactaacgt ctggaaagac gacaaaactt tagatcgtta cgctaactat gagggctgtc   1740
tgtggaatgc tacaggcgtt gtagtttgta ctggtgacga aactcagtgt tacggtacat   1800
gggttcctat tgggcttgct atccctgaaa atgagggtgg tggctctgag ggtggcggtt   1860
ctgagggtgg cggttctgag ggtggcggta ctaaacctcc tgagtacggt gatacaccta   1920
ttccgggcta tacttatatc aaccctctcg acggcactta tccgcctggt actgagcaaa   1980
accccgctaa tcctaatcct tctcttgagg agtctcagcc tcttaatact ttcatgtttc   2040
agaataatag gttccgaaat aggcaggggg cattaactgt ttatacgggc actgttactc   2100
aaggcactga ccccgttaaa acttattacc agtacactcc tgtatcatca aaagccatgt   2160
atgacgctta ctggaacggt aaattcagag actgcgcttt ccattctggc tttaatgagg   2220
atttatttgt ttgtgaatat caaggccaat cgtctgacct gcctcaacct cctgtcaatg   2280
ctggcggcgg ctctggtggt ggttctggtg gcggctctga gggtggtggc tctgagggtg   2340
```

-continued

```
gcggttctga gggtggcggc tctgagggag gcggttccgg tggtggctct ggttccggtg   2400
attttgatta tgaaaagatg gcaaacgcta ataagggggc tatgaccgaa aatgccgatg   2460
aaaacgcgct acagtctgac gctaaaggca aacttgattc tgtcgctact gattacggtg   2520
ctgctatcga tggtttcatt ggtgacgttt ccggccttgc taatggtaat ggtgctactg   2580
gtgattttgc tggctctaat tcccaaatgg ctcaagtcgg tgacggtgat aattcacctt   2640
taatgaataa tttccgtcaa tatttacctt ccctccctca atcggttgaa tgtcgccctt   2700
ttgtctttgg cgctggtaaa ccatatgaat tttctattga ttgtgacaaa ataaacttat   2760
tccgtggtgt ctttgcgttt cttttatatg ttgccacctt tatgtatgta ttttctacgt   2820
ttgctaacat actgcgtaat aaggagtctt aatcatgcca gttcttttgg gtattccgtt   2880
attattgcgt ttcctcggtt tccttctggt aactttgttc ggctatctgc ttacttttct   2940
taaaaagggc ttcggtaaga tagctattgc tatttcattg tttcttgctc ttattattgg   3000
gcttaactca attcttgtgg gttatctctc tgatattagc gctcaattac cctctgactt   3060
tgttcagggt gttcagttaa ttctcccgtc taatgcgctt ccctgttttt atgttattct   3120
ctctgtaaag gctgctattt tcatttttga cgttaaacaa aaaatcgttt cttatttgga   3180
ttgggataaa taatatggct gtttattttg taactggcaa attaggctct ggaaagacgc   3240
tcgttagcgt tggtaagatt caggataaaa ttgtagctgg gtgcaaaata gcaactaatc   3300
ttgatttaag gcttcaaaac ctcccgcaag tcgggaggtt cgctaaaacg cctcgcgttc   3360
ttagaatacc ggataagcct tctatatctg atttgcttgc tattgggcgc ggtaatgatt   3420
cctacgatga aaataaaaac ggcttgcttg ttctcgatga gtgcggtact tggtttaata   3480
cccgttcttg gaatgataag gaaagacagc cgattattga ttggtttcta catgctcgta   3540
aattaggatg ggatattatt tttcttgttc aggacttatc tattgttgat aaacaggcgc   3600
gttctgcatt agctgaacat gttgtttatt gtcgtcgtct ggacagaatt actttacctt   3660
ttgtcggtac tttatattct cttattactg gctcgaaaat gcctctgcct aaattacatg   3720
ttggcgttgt taaatatggc gattctcaat taagccctac tgttgagcgt tggctttata   3780
ctggtaagaa tttgtataac gcatatgata ctaaacaggc tttttctagt aattatgatt   3840
ccggtgttta ttcttattta acgccttatt tatcacacgg tcggtatttc aaaccattaa   3900
atttaggtca gaagatgaaa ttaactaaaa tatatttgaa aaagttttct cgcgttcttt   3960
gtcttgcgat tggatttgca tcagcattta catatagtta tataacccaa cctaagccgg   4020
aggttaaaaa ggtagtctct cagacctatg attttgataa attcactatt gactcttctc   4080
agcgtcttaa tctaagctat cgctatgttt tcaaggattc taagggaaaa ttaattaata   4140
gcgacgattt acagaagcaa ggttattcac tcacatatat tgatttatgt actgtttcca   4200
ttaaaaaagg taattcaaat gaaattgtta aatgtaatta attttgtttt cttgatgttt   4260
gtttcatcat cttcttttgc tcaggtaatt gaaatgaata attcgcctct gcgcgatttt   4320
gtaacttggt attcaaagca atcaggcgaa tccgttattg tttctcccga tgtaaaaggt   4380
actgttactg tatattcatc tgacgttaaa cctgaaaatc tacgcaattt ctttatttct   4440
gttttacgtg caaataattt tgatatggta ggttctaacc cttccattat tcagaagtat   4500
aatccaaaca atcaggatta tattgatgaa ttgccatcat ctgataatca ggaatatgat   4560
gataattccg ctccttctgg tggtttcttt gttccgcaaa atgataatgt tactcaaact   4620
tttaaaatta ataacgttcg ggcaaaggat ttaatacgag ttgtcgaatt gtttgtaaag   4680
tctaatactt ctaaatcctc aaatgtatta tctattgacg gctctaatct attagttgtt   4740
```

-continued

```
agtgctccta aagatatttt agataacctt cctcaattcc tttcaactgt tgatttgcca   4800
actgaccaga tattgattga gggtttgata tttgaggttc agcaaggtga tgctttagat   4860
ttttcatttg ctgctggctc tcagcgtggc actgttgcag gcggtgttaa tactgaccgc   4920
ctcacctctg ttttatcttc tgctggtggt tcgttcggta tttttaatgg cgatgtttta   4980
gggctatcag ttcgcgcatt aaagactaat agccattcaa aaatattgtc tgtgccacgt   5040
attcttacgc tttcaggtca gaagggttct atctctgttg gccagaatgt tccttttatt   5100
actggtcgtg tgactggtga atctgccaat gtaaataatc catttcagac gattgagcgt   5160
caaaatgtag gtatttccat gagcgttttt cctgttgcaa tggctggcgg taatattgtt   5220
ctggatatta ccagcaaggc cgatagtttg agttcttcta ctcaggcaag tgatgttatt   5280
actaatcaaa gaagtattgc tacaacggtt aatttgcgtg atggacagac tcttttactc   5340
ggtggcctca ctgattataa aaacacttct caggattctg gcgtaccgtt cctgtctaaa   5400
atccctttaa tcggcctcct gtttagctcc cgctctgatt ctaacgagga aagcacgtta   5460
tacgtgctcg tcaaagcaac catagtacgc gccctgtagc ggcgcattaa gcgcggcggg   5520
tgtggtggtt acgcgcagcg tgaccgctac acttgccagc gccctagcgc ccgctccttt   5580
cgctttcttc ccttcctttc tcgccacgtt cgccggcttt ccccgtcaag ctctaaatcg   5640
ggggctccct ttagggttcc gatttagtgc tttacggcac ctcgacccca aaaaacttga   5700
tttgggtgat ggttcacgta gtgggccatc gccctgatag acggtttttc gccctttgac   5760
gttggagtcc acgttcttta atagtggact cttgttccaa actggaacaa cactcaaccc   5820
tatctcgggc tattcttttg atttataagg gattttgccg atttcggaac caccatcaaa   5880
caggattttc gcctgctggg gcaaaccagc gtggaccgct tgctgcaact ctctcagggc   5940
caggcggtga agggcaatca gctgttgccc gtctcactgg tgaaaagaaa aaccaccctg   6000
gcgcccaata cgcaaaccgc ctctccccgc gcgttggccg attcattaat gcagctggca   6060
cgacaggttt cccgactgga aagcgggcag tgagcgcaac gcaattaatg tgagttagct   6120
cactcattag gcaccccagg ctttacactt tatgcttccg gctcgtatgt tgtgtggaat   6180
tgtgagcgga taacaatttc acacaggaaa cagctatgac catgattacg ccaagcttgc   6240
atgcctgcag gtcctcgaat tcactggccg tcgttttaca acgtcgtgac tgggaaaacc   6300
ctggcgttac ccaacttaat cgccttgcag cacatccccc tttcgccagc tggcgtaata   6360
gcgaagaggc ccgcaccgat cgcccttccc aacagttgcg cagcctgaat ggcgaatggc   6420
gctttgcctg gtttccggca ccagaagcgg tgccggaaag ctggctggag tgcgatcttc   6480
ctgaggccga tactgtcgtc gtcccctcaa actggcagat gcacggttac gatgcgccca   6540
tctacaccaa cgtgacctat cccattacgg tcaatccgcc gtttgttccc acggagaatc   6600
cgacgggttg ttactcgctc acatttaatg ttgatgaaag ctggctacag gaaggccaga   6660
cgcgaattat ttttgatggc gttcctattg gttaaaaaat gagctgattt aacaaaaatt   6720
taatgcgaat tttaacaaaa tattaacgtt tacaatttaa atatttgctt atacaatctt   6780
cctgtttttg gggcttttct gattatcaac cggggtacat atgattgaca tgctagtttt   6840
acgattaccg ttcatcgatt ctcttgtttg ctccagactc tcaggcaatg acctgatagc   6900
ctttgtagat ctctcaaaaa tagctaccct ctccggcatt aatttatcag ctagaacggt   6960
tgaatatcat attgatggtg atttgactgt ctccggcctt tctcaccctt ttgaatcttt   7020
acctacacat tactcaggca ttgcatttaa aatatatgag ggttctaaaa atttttatcc   7080
```

-continued ttgcgttgaa ataaaggctt ctcccgcaaa agtattacag ggtcataatg tttttggtac 7140
aaccgattta gctttatgct ctgaggcttt attgcttaat tttgctaatt ctttgccttg 7200
cctgtatgat ttattggatg tt 7222

<210> SEQ ID NO 2
<211> LENGTH: 7297
<212> TYPE: DNA
<213> ORGANISM: Artificial Sequence
<220> FEATURE:
<223> OTHER INFORMATION: Synthetic bacteriophage p7HPQp8RGDp3HPQ

<400> SEQUENCE: 2
cgcgccctgt agcggcgcat taagcgcggc gggtgtggtg gttacgcgca gcgtgaccgc 60
tacacttgcc agcgccctag cgcccgctcc tttcgctttc ttcccttcct ttctcgccac 120
gttcgccggc tttccccgtc aagctctaaa tcgggggctc cctttagggt tccgatttag 180
tgctttacgg cacctcgacc ccaaaaaact tgatttgggt gatggttcac gtagtgggcc 240
atcgccctga tagacggttt ttcgcccttt gacgttggag tccacgttct ttaatagtgg 300
actcttgttc caaactggaa caacactcaa ccctatctcg ggctattctt ttgatttata 360
agggattttg ccgatttcgg aaccaccatc aaacaggatt ttcgcctgct ggggcaaacc 420
agcgtggacc gcttgctgca actctctcag ggccaggcgg tgaagggcaa tcagctgttg 480
cccgtctcac tggtgaaaag aaaaaccacc ctggcgccca atacgcaaac cgcctctccc 540
cgcgcgttgg ccgattcatt aatgcagctg gcacgacagg tttcccgact ggaaagcggg 600
cagtgagcgc aacgcaatta atgtgagtta gctcactcat taggcacccc aggctttaca 660
ctttatgctt ccggctcgta tgttgtgtgg aattgtgagc ggataacaat ttcacacagg 720
aaacagctat gaccatgatt acgccaagct tgcatgcctg caggtcctcg aattcactgg 780
ccgtcgtttt acaacgtcgt gactgggaaa accctggcgt tacccaactt aatcgccttg 840
cagcacatcc ccctttcgcc agctggcgta atagcgaaga ggcccgcacc gatcgccctt 900
cccaacagtt gcgcagcctg aatggcgaat ggcgctttgc ctggtttccg gcaccagaag 960
cggtgccgga aagctggctg gagtgcgatc ttcctgaggc cgatactgtc gtcgtcccct 1020
caaactggca gatgcacggt tacgatgcgc ccatctacac caacgtgacc tatcccatta 1080
cggtcaatcc gccgtttgtt cccacggaga atccgacggg ttgttactcg ctcacattta 1140
atgttgatga aagctggcta caggaaggcc agacgcgaat tatttttgat ggcgttccta 1200
ttggttaaaa aatgagctga tttaacaaaa atttaatgcg aattttaaca aaatattaac 1260
gtttacaatt taaatatttg cttatacaat cttcctgttt ttggggcttt tctgattatc 1320
aaccggggta catatgattg acatgctagt tttacgatta ccgttcatcg attctcttgt 1380
ttgctccaga ctctcaggca atgacctgat agcctttgta gatctctcaa aaatagctac 1440
cctctccggc attaatttat cagctagaac ggttgaatat catattgatg gtgatttgac 1500
tgtctccggc ctttctcacc cttttgaatc tttacctaca cattactcag gcattgcatt 1560
taaaatatat gagggttcta aaaattttta tccttgcgtt gaaataaagg cttctcccgc 1620
aaaagtatta cagggtcata atgtttttgg tacaaccgat ttagctttat gctctgaggc 1680
tttattgctt aatttgcta attctttgcc ttgcctgtat gatttattgg atgttaatgc 1740
tactactatt agtagaattg atgccacctt ttcagctcgc gccccaaatg aaaatatagc 1800
taaacaggtt attgaccatt tgcgaaatgt atctaatggt caaactaaat ctactcgttc 1860
gcagaattgg gaatcaactg ttatatggaa tgaaacttcc agacaccgta ctttagttgc 1920

-continued atatttaaaa catgttgagc tacagcatta tattcagcaa ttaagctcta agccatccgc 1980
aaaaatgacc tcttatcaaa aggagcaatt aaaggtactc tctaatcctg acctgttgga 2040
gtttgcttcc ggtctggttc gctttgaagc tcgaattaaa acgcgatatt tgaagtcttt 2100
cgggcttcct cttaatcttt ttgatgcaat ccgctttgct tctgactata atagtcaggg 2160
taaagacctg atttttgatt tatggtcatt ctcgttttct gaactgttta aagcatttga 2220
gggggattca atgaatattt atgacgattc cgcagtattg gacgctatcc agtctaaaca 2280
ttttactatt accccctctg gcaaaacttc ttttgcaaaa gcctctcgct attttggttt 2340
ttatcgtcgt ctggtaaacg agggttatga tagtgttgct cttactatgc ctcgtaattc 2400
cttttggcgt tatgtatctg cattagttga atgtggtatt cctaaatctc aactgatgaa 2460
tctttctacc tgtaataatg ttgttccgtt agttcgtttt attaacgtag atttttcttc 2520
ccaacgtcct gactggtata atgagccagt tcttaaaatc gcataaggta attcacaatg 2580
attaaagttg aaattaaacc atctcaagcc caatttacta ctcgttctgg tgtttctcgt 2640
cagggcaagc cttattcact gaatgagcag ctttgttacg ttgatttggg taatgaatat 2700
ccggttcttg tcaagattac tcttgatgaa ggtcagccag cctatgcgcc tggtctgtac 2760
accgttcatc tgtcctcttt caaagttggt cagttcggtt cccttatgat tgaccgtctg 2820
cgcctcgttc cggctaagta acatggagtg cttgcatccg cagacttgtg tcgcggattt 2880
cgacacaatt tatcaggcga tgatacaaat ctccgttgta ctttgtttcg cgcttggtat 2940
aatcgctggg ggtcaaagat gagtgtttta gtgtattctt ttgcctcttt cgttttaggt 3000
tggtgccttc gtagtggcat tacgtatttt acccgtttaa tggaaacttc ctcatgaaaa 3060
agtctttagt cctcaaagcc tctgtagccg ttgctaccct cgttccgatg ctgtctttcg 3120
ctgcaggtgg ccgtggcgat tctgatgact atgatcccgc aaaagcggcc tttaactccc 3180
tgcaagcctc agcgaccgaa tatatcggtt atgcgtgggc gatggttgtt gtcattgtcg 3240
gcgcaactat cggtatcaag ctgtttaaga aattcacctc gaaagcaagc tgataaaccg 3300
atacaattaa aggctccttt tggagccttt tttttggaga ttttcaacgt gaaaaaatta 3360
ttattcgcaa ttcctttagt ggtacctttc tattctcact cggcgtgcca tccgcagggc 3420
ccgctgtgcg gcggtggatc ggccgaaact gttgaaagtt gtttagcaaa atcccataca 3480
gaaaattcat ttactaacgt ctggaaagac gacaaaactt tagatcgtta cgctaactat 3540
gagggctgtc tgtggaatgc tacaggcgtt gtagtttgta ctggtgacga aactcagtgt 3600
tacggtacat gggttcctat tgggcttgct atccctgaaa atgagggtgg tggctctgag 3660
ggtggcggtt ctgagggtgg cggttctgag ggtggcggta ctaaacctcc tgagtacggt 3720
gatacaccta ttccgggcta tacttatatc aaccctctcg acggcactta tccgcctggt 3780
actgagcaaa accccgctaa tcctaatcct tctcttgagg agtctcagcc tcttaatact 3840
ttcatgtttc agaataatag gttccgaaat aggcaggggg cattaactgt ttatacgggc 3900
actgttactc aaggcactga ccccgttaaa acttattacc agtacactcc tgtatcatca 3960
aaagccatgt atgacgctta ctggaacggt aaattcagag actgcgcttt ccattctggc 4020
tttaatgagg atttatttgt ttgtgaatat caaggccaat cgtctgacct gcctcaacct 4080
cctgtcaatg ctggcggcgg ctctggtggt ggttctggtg gcggctctga gggtggtggc 4140
tctgagggtg gcggttctga gggtggcggc tctgagggag gcggttccgg tggtggctct 4200
ggttccggtg attttgatta tgaaaagatg gcaaacgcta ataagggggc tatgaccgaa 4260

-continued

```
aatgccgatg aaaacgcgct acagtctgac gctaaaggca aacttgattc tgtcgctact   4320
gattacggtg ctgctatcga tggtttcatt ggtgacgttt ccggccttgc taatggtaat   4380
ggtgctactg gtgattttgc tggctctaat tcccaaatgg ctcaagtcgg tgacggtgat   4440
aattcacctt taatgaataa tttccgtcaa tatttacctt ccctccctca atcggttgaa   4500
tgtcgccctt ttgtctttgg cgctggtaaa ccatatgaat tttctattga ttgtgacaaa   4560
ataaacttat tccgtggtgt ctttgcgttt cttttatatg ttgccacctt tatgtatgta   4620
ttttctacgt ttgctaacat actgcgtaat aaggagtctt aatcatgcca gttcttttgg   4680
gtattccgtt attattgcgt ttcctcggtt tccttctggt aactttgttc ggctatctgc   4740
ttacttttct taaaaagggc ttcggtaaga tagctattgc tatttcattg tttcttgctc   4800
ttattattgg gcttaactca attcttgtgg gttatctctc tgatattagc gctcaattac   4860
cctctgactt tgttcagggt gttcagttaa ttctcccgtc taatgcgctt ccctgttttt   4920
atgttattct ctctgtaaag gctgctattt tcatttttga cgttaaacaa aaaatcgttt   4980
cttatttgga ttgggataaa taatatggct gtttattttg taactggcaa attaggctct   5040
ggaaagacgc tcgttagcgt tggtaagatt caggataaaa ttgtagctgg gtgcaaaata   5100
gcaactaatc ttgatttaag gcttcaaaac ctcccgcaag tcgggaggtt cgctaaaacg   5160
cctcgcgttc ttagaatacc ggataagcct tctatatctg atttgcttgc tattgggcgc   5220
ggtaatgatt cctacgatga aaataaaaac ggcttgcttg ttctcgatga gtgcggtact   5280
tggtttaata cccgttcttg gaatgataag gaaagacagc cgattattga ttggtttcta   5340
catgctcgta aattaggatg ggatattatt tttcttgttc aggacttatc tattgttgat   5400
aaacaggcgc gttctgcatt agctgaacat gttgtttatt gtcgtcgtct ggacagaatt   5460
actttacctt ttgtcggtac tttatattct cttattactg gctcgaaaat gcctctgcct   5520
aaattacatg ttggcgttgt taaatatggc gattctcaat taagccctac tgttgagcgt   5580
tggctttata ctggtaagaa tttgtataac gcatatgata ctaaacaggc tttttctagt   5640
aattatgatt ccggtgttta ttcttattta acgccttatt tatcacacgg tcggtatttc   5700
aaaccattaa atttaggtca gaagatgaaa ttaactaaaa tatatttgaa aaagttttct   5760
cgcgttcttt gtcttgcgat tggatttgca tcagcattta catatagtta tataacccaa   5820
cctaagccgg aggttaaaaa ggtagtctct cagacctatg attttgataa attcactatt   5880
gactcttctc agcgtcttaa tctaagctat cgctatgttt tcaaggattc taagggaaaa   5940
ttaattaata gcgacgattt acagaagcaa ggttattcac tcacatatat tgatttatgt   6000
actgtttcca ttaaaaaagg taattcaaat gaaattgtta aatgtaatta attttgtttt   6060
cttgatgttt gtttcatcat cttcttttgc tcaggtaatt gaaatgaata attcgcctct   6120
gcgcgatttt gtaacttggt attcaaagca atcaggcgaa tccgttattg tttctcccga   6180
tgtaaaaggt actgttactg tatattcatc tgacgttaaa cctgaaaatc tacgcaattt   6240
ctttatttct gttttacgtg caaataattt tgatatggta ggttctaacc cttccattat   6300
tcagaagtat aatccaaaca atcaggatta tattgatgaa ttgccatcat ctgataatca   6360
ggaatatgat gataattccg ctccttctgg tggtttcttt gttccgcaaa atgataatgt   6420
tactcaaact tttaaaatta ataacgttcg ggcaaaggat ttaatacgag ttgtcgaatt   6480
gtttgtaaag tctaatactt ctaaatcctc aaatgtatta tctattgacg gctctaatct   6540
attagttgtt agtgctccta aagatatttt agataacctt cctcaattcc tttcaactgt   6600
tgatttgcca actgaccaga tattgattga gggtttgata tttgaggttc agcaaggtga   6660
```

```
tgctttagat ttttcatttg ctgctggctc tcagcgtggc actgttgcag gcggtgttaa   6720

tactgaccgc ctcacctctg ttttatcttc tgctggtggt tcgttcggta tttttaatgg   6780

cgatgtttta gggctatcag ttcgcgcatt aaagactaat agccattcaa aaatattgtc   6840

tgtgccacgt attcttacgc tttcaggtca gaagggttct atctctgttg gccagaatgt   6900

tccttttatt actggtcgtg tgactggtga atctgccaat gtaaataatc catttcagac   6960

gattgagcgt caaaatgtag gtatttccat gagcgttttt cctgttgcaa tggctggcgg   7020

taatattgtt ctggatatta ccagcaaggc cgatagtttg agttcttcta ctcaggcaag   7080

tgatgttatt actaatcaaa gaagtattgc tacaacggtt aatttgcgtg atggacagac   7140

tcttttactc ggtggcctca ctgattataa aaacacttct caggattctg gcgtaccgtt   7200

cctgtctaaa atccctttaa tcggcctcct gtttagctcc cgctctgatt ctaacgagga   7260

aagcacgtta tacgtgctcg tcaaagcaac catagta                            7297
```

<210> SEQ ID NO 3
<211> LENGTH: 7295
<212> TYPE: DNA
<213> ORGANISM: Artificial Sequence
<220> FEATURE:
<223> OTHER INFORMATION: Synthetic bacteriophage p9HPQp8RGDp3HPQ

<400> SEQUENCE: 3

```
cgcgccctgt agcggcgcat taagcgcggc gggtgtggtg gttacgcgca gcgtgaccgc     60

tacacttgcc agcgccctag cgcccgctcc tttcgctttc ttcccttcct ttctcgccac    120

gttcgccggc tttccccgtc aagctctaaa tcgggggctc cctttagggt tccgatttag    180

tgctttacgg cacctcgacc ccaaaaaact tgatttgggt gatggttcac gtagtgggcc    240

atcgccctga tagacggttt ttcgcccttt gacgttggag tccacgttct ttaatagtgg    300

actcttgttc caaactggaa caacactcaa ccctatctcg ggctattctt ttgatttata    360

agggattttg ccgatttcgg aaccaccatc aaacaggatt ttcgcctgct ggggcaaacc    420

agcgtggacc gcttgctgca actctctcag ggccaggcgg tgaagggcaa tcagctgttg    480

cccgtctcac tggtgaaaag aaaaaccacc ctggcgccca atacgcaaac cgcctctccc    540

cgcgcgttgg ccgattcatt aatgcagctg gcacgacagg tttcccgact ggaaagcggg    600

cagtgagcgc aacgcaatta atgtgagtta gctcactcat taggcacccc aggctttaca    660

ctttatgctt ccggctcgta tgttgtgtgg aattgtgagc ggataacaat ttcacacagg    720

aaacagctat gaccatgatt acgccaagct tgcatgcctg caggtcctcg aattcactgg    780

ccgtcgtttt acaacgtcgt gactgggaaa accctggcgt tacccaactt aatcgccttg    840

cagcacatcc ccctttcgcc agctggcgta atagcgaaga ggcccgcacc gatcgccctt    900

cccaacagtt gcgcagcctg aatggcgaat ggcgctttgc ctggtttccg gcaccagaag    960

cggtgccgga aagctggctg gagtgcgatc ttcctgaggc cgatactgtc gtcgtcccct   1020

caaactggca gatgcacggt tacgatgcgc ccatctacac caacgtgacc tatcccatta   1080

cggtcaatcc gccgtttgtt cccacggaga atccgacggg ttgttactcg ctcacattta   1140

atgttgatga aagctggcta caggaaggcc agacgcgaat tatttttgat ggcgttccta   1200

ttggttaaaa aatgagctga tttaacaaaa atttaatgcg aattttaaca aaatattaac   1260

gtttacaatt taaatatttg cttatacaat cttcctgttt ttggggcttt tctgattatc   1320

aaccggggta catatgattg acatgctagt tttacgatta ccgttcatcg attctcttgt   1380
```

-continued

```
ttgctccaga ctctcaggca atgacctgat agcctttgta gatctctcaa aaatagctac   1440
cctctccggc attaatttat cagctagaac ggttgaatat catattgatg gtgatttgac   1500
tgtctccggc ctttctcacc cttttgaatc tttacctaca cattactcag gcattgcatt   1560
taaaatatat gagggttcta aaaattttta tccttgcgtt gaaataaagg cttctcccgc   1620
aaaagtatta cagggtcata atgtttttgg tacaaccgat ttagctttat gctctgaggc   1680
tttattgctt aattttgcta attctttgcc ttgcctgtat gatttattgg atgttaatgc   1740
tactactatt agtagaattg atgccacctt ttcagctcgc gccccaaatg aaaatatagc   1800
taaacaggtt attgaccatt tgcgaaatgt atctaatggt caaactaaat ctactcgttc   1860
gcagaattgg gaatcaactg ttatatggaa tgaaacttcc agacaccgta ctttagttgc   1920
atatttaaaa catgttgagc tacagcatta tattcagcaa ttaagctcta agccatccgc   1980
aaaaatgacc tcttatcaaa aggagcaatt aaaggtactc tctaatcctg acctgttgga   2040
gtttgcttcc ggtctggttc gctttgaagc tcgaattaaa acgcgatatt tgaagtcttt   2100
cgggcttcct cttaatcttt ttgatgcaat ccgctttgct tctgactata atagtcaggg   2160
taaagacctg atttttgatt tatggtcatt ctcgttttct gaactgttta aagcatttga   2220
gggggattca atgaatattt atgacgattc cgcagtattg gacgctatcc agtctaaaca   2280
ttttactatt accccctctg gcaaaacttc ttttgcaaaa gcctctcgct attttggttt   2340
ttatcgtcgt ctggtaaacg agggttatga tagtgttgct cttactatgc ctcgtaattc   2400
cttttggcgt tatgtatctg cattagttga atgtggtatt cctaaatctc aactgatgaa   2460
tctttctacc tgtaataatg ttgttccgtt agttcgtttt attaacgtag atttttcttc   2520
ccaacgtcct gactggtata atgagccagt tcttaaaatc gcataaggta attcacaatg   2580
attaaagttg aaattaaacc atctcaagcc caatttacta ctcgttctgg tgtttctcgt   2640
cagggcaagc cttattcact gaatgagcag ctttgttacg ttgatttggg taatgaatat   2700
ccggttcttg tcaagattac tcttgatgaa ggtcagccag cctatgcgcc tggtctgtac   2760
accgttcatc tgtcctcttt caaagttggt cagttcggtt cccttatgat tgaccgtctg   2820
cgcctcgttc cggctaagta acatggagca ggtcgcggat ttcgacacaa tttatcaggc   2880
gatgatacaa atctccgttg tactttgttt cgcgcttggt ataatcgctg ggggtcaaag   2940
atgagtgttt tagtgtattc ttttgcctct ttcgttttag gttggtgcct tcgtagtggc   3000
attacgtatt ttacccgttt aatggaaact tcccatccgc agagctgact catgaaaaag   3060
tctttagtcc tcaaagcctc tgtagccgtt gctaccctcg ttccgatgct gtctttcgct   3120
gcaggtggcc gtggcgattc tgatgactat gatcccgcaa aagcggcctt taactccctg   3180
caagcctcag cgaccgaata tatcggttat gcgtgggcga tggttgttgt cattgtcggc   3240
gcaactatcg gtatcaagct gtttaagaaa ttcacctcga aagcaagctg ataaaccgat   3300
acaattaaag gctccttttg gagccttttt tttggagatt ttcaacgtga aaaaattatt   3360
attcgcaatt cctttagtgg tacctttcta ttctcactcg gcgtgccatc cgcagggccc   3420
gctgtgcggc ggtggatcgg ccgaaactgt tgaaagttgt ttagcaaaat cccatacaga   3480
aaattcattt actaacgtct ggaaagacga caaaacttta gatcgttacg ctaactatga   3540
gggctgtctg tggaatgcta caggcgttgt agtttgtact ggtgacgaaa ctcagtgtta   3600
cggtacatgg gttcctattg ggcttgctat ccctgaaaat gagggtggtg gctctgaggg   3660
tggcggttct gagggtggcg gttctgaggg tggcggtact aaacctcctg agtacggtga   3720
tacacctatt ccgggctata cttatatcaa ccctctcgac ggcacttatc cgcctggtac   3780
```

```
tgagcaaaac cccgctaatc ctaatccttc tcttgaggag tctcagcctc ttaatacttt   3840
catgtttcag aataataggt tccgaaatag gcagggggca ttaactgttt atacgggcac   3900
tgttactcaa ggcactgacc ccgttaaaac ttattaccag tacactcctg tatcatcaaa   3960
agccatgtat gacgcttact ggaacggtaa attcagagac tgcgctttcc attctggctt   4020
taatgaggat ttatttgttt gtgaatatca aggccaatcg tctgacctgc ctcaacctcc   4080
tgtcaatgct ggcggcggct ctggtggtgg ttctggtggc ggctctgagg gtggtggctc   4140
tgagggtggc ggttctgagg gtggcggctc tgagggaggc ggttccggtg gtggctctgg   4200
ttccggtgat tttgattatg aaaagatggc aaacgctaat aagggggcta tgaccgaaaa   4260
tgccgatgaa aacgcgctac agtctgacgc taaaggcaaa cttgattctg tcgctactga   4320
ttacggtgct gctatcgatg gtttcattgg tgacgtttcc ggccttgcta atggtaatgg   4380
tgctactggt gattttgctg gctctaattc ccaaatggct caagtcggtg acggtgataa   4440
ttcaccttta atgaataatt tccgtcaata tttaccttcc ctccctcaat cggttgaatg   4500
tcgccctttt gtctttggcg ctggtaaacc atatgaattt tctattgatt gtgacaaaat   4560
aaacttattc cgtggtgtct ttgcgtttct tttatatgtt gccaccttta tgtatgtatt   4620
ttctacgttt gctaacatac tgcgtaataa ggagtcttaa tcatgccagt tcttttgggt   4680
attccgttat tattgcgttt cctcggtttc cttctggtaa ctttgttcgg ctatctgctt   4740
acttttctta aaaagggctt cggtaagata gctattgcta tttcattgtt tcttgctctt   4800
attattgggc ttaactcaat tcttgtgggt tatctctctg atattagcgc tcaattaccc   4860
tctgactttg ttcagggtgt tcagttaatt ctcccgtcta atgcgcttcc ctgtttttat   4920
gttattctct ctgtaaaggc tgctattttc atttttgacg ttaaacaaaa aatcgtttct   4980
tatttggatt gggataaata atatggctgt ttattttgta actggcaaat taggctctgg   5040
aaagacgctc gttagcgttg gtaagattca ggataaaatt gtagctgggt gcaaaatagc   5100
aactaatctt gatttaaggc ttcaaaacct cccgcaagtc gggaggttcg ctaaaacgcc   5160
tcgcgttctt agaataccgg ataagccttc tatatctgat ttgcttgcta ttgggcgcgg   5220
taatgattcc tacgatgaaa ataaaaacgg cttgcttgtt ctcgatgagt gcggtacttg   5280
gtttaatacc cgttcttgga atgataagga aagacagccg attattgatt ggtttctaca   5340
tgctcgtaaa ttaggatggg atattatttt tcttgttcag gacttatcta ttgttgataa   5400
acaggcgcgt tctgcattag ctgaacatgt tgtttattgt cgtcgtctgg acagaattac   5460
tttacctttt gtcggtactt tatattctct tattactggc tcgaaaatgc ctctgcctaa   5520
attacatgtt ggcgttgtta aatatggcga ttctcaatta agccctactg ttgagcgttg   5580
gctttatact ggtaagaatt tgtataacgc atatgatact aaacaggctt tttctagtaa   5640
ttatgattcc ggtgtttatt cttatttaac gccttattta tcacacggtc ggtatttcaa   5700
accattaaat ttaggtcaga agatgaaatt aactaaaata tatttgaaaa agttttctcg   5760
cgttctttgt cttgcgattg gatttgcatc agcatttaca tatagttata taacccaacc   5820
taagccggag gttaaaaagg tagtctctca gacctatgat tttgataaat tcactattga   5880
ctcttctcag cgtcttaatc taagctatcg ctatgttttc aaggattcta agggaaaatt   5940
aattaatagc gacgatttac agaagcaagg ttattcactc acatatattg atttatgtac   6000
tgtttccatt aaaaaaggta attcaaatga aattgttaaa tgtaattaat tttgttttct   6060
tgatgtttgt ttcatcatct tcttttgctc aggtaattga aatgaataat tcgcctctgc   6120
```

-continued gcgattttgt aacttggtat tcaaagcaat caggcgaatc cgttattgtt tctcccgatg 6180
taaaaggtac tgttactgta tattcatctg acgttaaacc tgaaaatcta cgcaatttct 6240
ttatttctgt tttacgtgca aataattttg atatggtagg ttctaaccct tccattattc 6300
agaagtataa tccaaacaat caggattata ttgatgaatt gccatcatct gataatcagg 6360
aatatgatga taattccgct ccttctggtg gtttctttgt tccgcaaaat gataatgtta 6420
ctcaaacttt taaaattaat aacgttcggg caaaggattt aatacgagtt gtcgaattgt 6480
ttgtaaagtc taatacttct aaatcctcaa atgtattatc tattgacggc tctaatctat 6540
tagttgttag tgctcctaaa gatattttag ataaccttcc tcaattcctt tcaactgttg 6600
atttgccaac tgaccagata ttgattgagg gtttgatatt tgaggttcag caaggtgatg 6660
ctttagattt ttcatttgct gctggctctc agcgtggcac tgttgcaggc ggtgttaata 6720
ctgaccgcct cacctctgtt ttatcttctg ctggtggttc gttcggtatt tttaatggcg 6780
atgttttagg gctatcagtt cgcgcattaa agactaatag ccattcaaaa atattgtctg 6840
tgccacgtat tcttacgctt tcaggtcaga agggttctat ctctgttggc cagaatgttc 6900
cttttattac tggtcgtgtg actggtgaat ctgccaatgt aaataatcca tttcagacga 6960
ttgagcgtca aaatgtaggt atttccatga gcgtttttcc tgttgcaatg gctggcggta 7020
atattgttct ggatattacc agcaaggccg atagtttgag ttcttctact caggcaagtg 7080
atgttattac taatcaaaga agtattgcta caacggttaa tttgcgtgat ggacagactc 7140
ttttactcgg tggcctcact gattataaaa acacttctca ggattctggc gtaccgttcc 7200
tgtctaaaat ccctttaatc ggcctcctgt ttagctcccg ctctgattct aacgaggaaa 7260
gcacgttata cgtgctcgtc aaagcaacca tagta 7295

<210> SEQ ID NO 4
<211> LENGTH: 65
<212> TYPE: DNA
<213> ORGANISM: Artificial Sequence
<220> FEATURE:
<223> OTHER INFORMATION: primer p8-RDDD Fw
<220> FEATURE:
<221> NAME/KEY: misc_feature
<222> LOCATION: (13)..(14)
<223> OTHER INFORMATION: n = A, T, C, or G

<400> SEQUENCE: 4
atatatctgc agnnggccgt ggcgattctg atgacgatga tcccgcaaaa gcggccttta 60
atccc 65

<210> SEQ ID NO 5
<211> LENGTH: 25
<212> TYPE: DNA
<213> ORGANISM: Artificial Sequence
<220> FEATURE:
<223> OTHER INFORMATION: primer p8-rev1376

<400> SEQUENCE: 5
cctctgcagc gaaagacagc atcgg 25

<210> SEQ ID NO 6
<211> LENGTH: 35
<212> TYPE: DNA
<213> ORGANISM: Artificial Sequence
<220> FEATURE:
<223> OTHER INFORMATION: primer p3-Fwd1626

<400> SEQUENCE: 6

-continued aaacactcgg ccgaaactgt tgaaagttgt ttagc 35

<210> SEQ ID NO 7
<211> LENGTH: 83
<212> TYPE: DNA
<213> ORGANISM: Artificial Sequence
<220> FEATURE:
<223> OTHER INFORMATION: primer p3-rev RGD

<400> SEQUENCE: 7
tatatacggc cgatccaccg ccgcagctat cgccacggcc gcacgccgag tgagaataga 60
aaggaaccac taaaggaatt gcg 83

<210> SEQ ID NO 8
<211> LENGTH: 42
<212> TYPE: DNA
<213> ORGANISM: Artificial Sequence
<220> FEATURE:
<223> OTHER INFORMATION: primer Fw-BspHI-p9

<400> SEQUENCE: 8
aaacactcat gaaaaagtct ttagtcctca aagcctctgt ag 42

<210> SEQ ID NO 9
<211> LENGTH: 46
<212> TYPE: DNA
<213> ORGANISM: Artificial Sequence
<220> FEATURE:
<223> OTHER INFORMATION: primer Re-BspHI-HPQ-p9
<220> FEATURE:
<221> NAME/KEY: misc_feature
<222> LOCATION: (13)..(13)
<223> OTHER INFORMATION: n = A, T, C, or G

<400> SEQUENCE: 9
tatatatcat gantcagctc tgcggatggg aagtttccat taaacg 46

<210> SEQ ID NO 10
<211> LENGTH: 57
<212> TYPE: DNA
<213> ORGANISM: Artificial Sequence
<220> FEATURE:
<223> OTHER INFORMATION: primer Re-BspHI-XXHPQXXS-p9
<220> FEATURE:
<221> NAME/KEY: misc_feature
<222> LOCATION: (13)..(40)
<223> OTHER INFORMATION: n = A, T, C, or G

<400> SEQUENCE: 10
tatatatcat gantcagctm nnmnnctgcg gatgmnnmnn ggaagtttcc attaacg 57

<210> SEQ ID NO 11
<211> LENGTH: 54
<212> TYPE: DNA
<213> ORGANISM: Artificial Sequence
<220> FEATURE:
<223> OTHER INFORMATION: primer BamHI- N-HPQ Fw p7

<400> SEQUENCE: 11
atatatggat ccatggagca tccgcaggtc gcggatttcg acacaattta tcag 54

<210> SEQ ID NO 12
<211> LENGTH: 42
<212> TYPE: DNA
<213> ORGANISM: Artificial Sequence
<220> FEATURE:

-continued

```
<223> OTHER INFORMATION: primer BamHI-N-HPQ Re p7

<400> SEQUENCE: 12

aaacacggat ccgttactta gccggaacga ggcgcagacg gt                    42


<210> SEQ ID NO 13
<211> LENGTH: 57
<212> TYPE: DNA
<213> ORGANISM: Artificial Sequence
<220> FEATURE:
<223> OTHER INFORMATION: primer BamHI- N-HPQ Fw p9

<400> SEQUENCE: 13

atatatggat ccatgagtca tccgcaggtt ttagtgtatt cttttgcctc tttcgtt    57


<210> SEQ ID NO 14
<211> LENGTH: 41
<212> TYPE: DNA
<213> ORGANISM: Artificial Sequence
<220> FEATURE:
<223> OTHER INFORMATION: primer BamHI- N-HPQ Re p9

<400> SEQUENCE: 14

aaacacggat ccctttgacc cccagcgatt ataccaagcg c                     41

<210> SEQ ID NO 15
<211> LENGTH: 66
<212> TYPE: DNA
<213> ORGANISM: Artificial Sequence
<220> FEATURE:
<223> OTHER INFORMATION: primer BamHI- cir N-HPQ Fw p7
<220> FEATURE:
<221> NAME/KEY: misc_feature
<222> LOCATION: (22)..(35)
<223> OTHER INFORMATION: n = A, T, C, or G

<400> SEQUENCE: 15

atatatggat ccatggagtg cnnkcatccg cagnnktgtg tcgcggattt cgacacaatt  60

tatcag                                                             66

<210> SEQ ID NO 16
<211> LENGTH: 68
<212> TYPE: DNA
<213> ORGANISM: Artificial Sequence
<220> FEATURE:
<223> OTHER INFORMATION: primer BamHI- cir N-HPQ Fw p9
<220> FEATURE:
<221> NAME/KEY: misc_feature
<222> LOCATION: (21)..(34)
<223> OTHER INFORMATION: n = A, T, C, or G

<400> SEQUENCE: 16

tatatggatc catgagttgc nnkcatccgc agnnktgtgt tttagtgtat tcttttgcct  60

ctttcgtt                                                           68
```